(12) United States Patent
Foster et al.

(10) Patent No.: US 11,917,993 B2
(45) Date of Patent: Mar. 5, 2024

(54) ANTIMICROBIAL COMPOSITIONS

(71) Applicant: LANXESS Corporation, Pittsburgh, PA (US)

(72) Inventors: Stephen Finley Foster, Ridgefield, WA (US); Kelly Reed Pippine, Vancouver, WA (US); James Anthony Proestos, Jr., Portland, OR (US); Bradley Les Farrell, Vancouver, WA (US); Julie O. Vaughn-Biege, Copley, OH (US)

(73) Assignee: LANXESS Corporation, Pittsburgh, PA (US)

( * ) Notice: Subject to any disclaimer, the term of this patent is extended or adjusted under 35 U.S.C. 154(b) by 22 days.

(21) Appl. No.: 16/760,971

(22) PCT Filed: Nov. 2, 2018

(86) PCT No.: PCT/US2018/058995
§ 371 (c)(1),
(2) Date: May 1, 2020

(87) PCT Pub. No.: WO2019/090105
PCT Pub. Date: May 9, 2019

(65) Prior Publication Data
US 2020/0296958 A1 Sep. 24, 2020

Related U.S. Application Data

(60) Provisional application No. 62/581,335, filed on Nov. 3, 2017.

(51) Int. Cl.
*A01N 31/02* (2006.01)
*A01N 31/04* (2006.01)
*A01N 37/10* (2006.01)

(52) U.S. Cl.
CPC ............ *A01N 31/02* (2013.01); *A01N 31/04* (2013.01); *A01N 37/10* (2013.01)

(58) Field of Classification Search
CPC ......... A01N 31/02; A01N 31/04; A01N 37/10
See application file for complete search history.

(56) References Cited

U.S. PATENT DOCUMENTS

| | | | |
|---|---|---|---|
| 4,711,914 A | 8/1987 | Rei et al. | |
| 4,721,736 A | 1/1988 | Rei et al. | |
| 6,120,758 A | 9/2000 | Siddiqui et al. | |
| 7,537,776 B1 | 5/2009 | Beilfuss et al. | |
| 8,501,206 B2 | 8/2013 | Beilfuss et al. | |
| 8,784,910 B2 | 7/2014 | Lutz et al. | |
| 9,596,849 B2 | 3/2017 | Klug | |
| 2012/0210523 A1 | 8/2012 | Lalleman et al. | |
| 2016/0001503 A1* | 1/2016 | Tsai | B33Y 30/00 264/40.7 |
| 2016/0015031 A1* | 1/2016 | Pesaro | A01N 35/04 514/689 |
| 2016/0353752 A1 | 12/2016 | Stinson et al. | |
| 2018/0068825 A1 | 3/2018 | Brodie | |

FOREIGN PATENT DOCUMENTS

| | | |
|---|---|---|
| EP | 3023090 A1 | 5/2016 |
| EP | 3332642 A1 | 6/2018 |
| WO | 0128332 A1 | 4/2001 |
| WO | 2007071089 A1 | 6/2007 |
| WO | 2011141462 A1 | 11/2011 |
| WO | 2014009157 A1 | 1/2014 |
| WO | 2014135650 A1 | 9/2014 |
| WO | 2014191258 A2 | 12/2014 |
| WO | 2015090634 A1 | 6/2015 |
| WO | 2016054021 A1 | 4/2016 |
| WO | 2016084078 A1 | 6/2016 |
| WO | 2016164555 A1 | 10/2016 |
| WO | 2017116445 A1 | 7/2017 |

OTHER PUBLICATIONS

Romano, DF et al. Recombinant *S. cerevisiae* expressing Old Yellow Enzymes from non-conventional yeasts: an easy system for selective reduction of activated alkenes. Microbial Cell Factories, vol. 13, 2014, 60, pp. 1-10; p. 2, col. 2, paragraph 3.
Supplemental European Search Report from corresponding European Application No. 18873049.3, dated Aug. 12, 2021, five pages.
Miralles Pablo, et al: "Determination of alternative preservatives in cosmetic products by chromophoric derivatization followed by vortex-assisted liquid-liquid semimicroextraction and liquid chromatography", TALANTA, vol. 154, (Jul. 1, 2016) pp. 1-6.
Richards R M E, et al: "Enhancement of Benzalkonium Chloride and Chlorhexidine Acetate Activity against Pseudomonas aeruginosa by Aromatic Alcohols", Journal of Pharmaceutical Sciences, American Chemical Society and American Pharmaceutical Association. vol. 62. No. 12, (Dec. 1, 1973) pp. 2035-2037.
Olonisakin A, et al: "Composition and antibacteria activity of steam distilled oils from Xylopia aethiopica and Syzgium aromati cum", Journal of Engineering and Applied Sciences. Medwell Publications. Faisalabad. Pakistan (Jan. 1, 2007) pp. 236-210.
Vukovic Nenad: "Antimicrobial Activity of the Essential Oil Obtained from Roots and Chemical Composition of the Volatile Constituents from the Roots, Stems, and Leaves of Ballota nigra from Serbia", J. Med. Food, vol. 12, No. 3, (Aug. 3, 2008) pp. 435-441.
Ma Xiao-Jing: "GC-MS Analysis of Volatile 1-4 Components of Alpiniae Oxyphylla Fructus Produced in Hainan Province Before and After Being Processed with Salt", Chinese Journal of Experimental Traditional Medical Formulae, vol. 21, No. 16, (Aug. 1, 2015) pp. 28-31.

(Continued)

*Primary Examiner* — Yong L Chu
(74) *Attorney, Agent, or Firm* — Nicanor A. Kohncke; Christopher L. McDavid; Ewa M. Wozniak

(57) ABSTRACT

An antimicrobial composition comprising 3-phenyl propanol or 2-methyl 3-phenylpropanol, or mixtures thereof, alone or in combination with an organic acid or salt thereof, or an alcohol, or mixtures thereof. Methods of preserving products and end-use applications for use of the inventive antimicrobial compositions are also provided.

3 Claims, 14 Drawing Sheets

(56) References Cited

OTHER PUBLICATIONS

Braun, et al: "Synthesen in der fettaromatischen Reihe IX", Berichte Der Deutschen Chemischen Gesellschaft, vol. 46, No. 2, (Jun. 30, 1913) pp. 1266-1282.

Anonymous: "CosIng—Cosmetics—GROWTH—European Commission", (Jul. 17, 2021), XP055825301, Retrieved from the Internet: URL:https:jjec.europa.eujgrowthjtools-data basesjcosingjindex.cfm?fuseaction=search details v2&id=79707 [retrieved on Jul. 17, 2021].

Anonymous: "CosIng—Cosmetics—GROWTH—European Commission", (Jul. 17, 2021), XP055825302, Retrieved from the Internet: URL:https:jjec.europa.eujgrowthjtools-data basesjcosingjindex.cfm?fuseaction=search details v2&id=32153 [retrieved on Jul. 17, 2021].

Mizobuchi Tomonori, et al: "Evaluation of antimicrobial activities of fragrance ingredients", Gakkaishi [Journal of Japanese Cosmetic Science Society]. Nippon Koshohin Gakkai, vol. 32, No. 2, (Jan. 1, 2008) pp. 95-111.

Cetearyl, et al: "Final Report on the Safety Assessment of Cetearyl Alcohol, Cetyl Alcohol, Isostearyl Alcohol, Myristyl Alcohol, and Behenyl Alcohol", International Journal of Toxicology, (May 1, 1988), pp. 359-413.

Mackie M.A, et al: "Antimicrobial properties of some aromatic alcohols", Pharmaceutica Acta Helvetiae, Elsevier BV Netherlands, vol. 61, No. 12, (Jan. 1, 1986) pp. 333-336.

Richards R M E et al: "Preliminary investigation of the preservative properties of 3-phenylpropanol", Pharmaceutical and Clinical Research, John Wiley & Sons Ltd. London, GB, vol. 24, Supp 1, (Jan. 1, 1972) pp. 158P-159P.

International Search Report from corresponding International Application No. PCT/US2018/058995, dated Dec. 26, 2018, three pages.

European Search Opinion from corresponding European Application No. 18873049.3, dated Aug. 30, 2021, 15 pages.

* cited by examiner

ANTIMICROBIAL COMPOSITIONS

FIELD OF THE INVENTION

This invention is directed to compositions having broad spectrum antimicrobial activity against a wide variety of microorganisms comprising 3-phenyl propanol or 2-methyl-3-phenyl propanol, or mixtures thereof, alone or in combination with organic acids or salts thereof and/or alcohols. The invention is also directed to concentrated blends of antimicrobial components and to end use compositions comprising the antimicrobial compositions of the invention.

BACKGROUND OF THE INVENTION

Many components of personal care, cosmetic, household products, healthcare products, industrial products, pharmaceutical products, and consumer products provide viable growth medium for microorganisms. This is especially prevalent in water-based, or aqueous, compositions. As such, addition of antimicrobial compositions to a wide variety of products is highly desirable to prevent or deter growth of microorganisms and maintain the integrity of the products when used over time or in storage.

Ideally, an antimicrobial composition maintains activity over the useful life of the product. Some antimicrobial compounds may be effective when used alone, while others have low or minimal antimicrobial effects and are used in combination with other antimicrobial compounds to enhance the antimicrobial activity. Efficacy of an antimicrobial for any particular application may vary and ultimately be dependent upon the amount used, the product formulation, and the presence of other compounds in the formulation.

Preservative compositions utilizing antimicrobial compounds are known in the art. Preservative compositions, optimally, provide a wide range of coverage against various microorganisms, including without limitation bacteria, fungi, mold, yeast, protozoa, and viruses. Compositions exhibiting a wide range of coverage, i.e., broad spectrum coverage, are highly desirable.

Traditional preservatives for use in personal care, cosmetics, toiletries and household products include but are not limited to ethanol, propanol, quaternium compounds, quaternary ammonium compounds, chlorhexidine, triclosan, acetophenones, benzyl alcohol, parabens; isothiazolonones, formaldehydes, cinnamaldehyde, sorbic acid and salts thereof, benzoic acid and salts thereof, ureas, hydantoins, and mixtures thereof, among many others. There are increasing concerns about the health and safety of certain of these traditional preservatives. Recently, there has been heightened emphasis on the use of natural or nature identical compounds having antimicrobial effects, such as natural or essential oils or other compounds found in nature.

Amounts of typical preservative compounds utilized to achieve antimicrobial effects in a product vary. Some compounds are highly effective at low concentrations, while others require a much higher concentration to achieve the same effects. Still other compounds may require addition of other compounds to reach full effect. Preservative compositions may be used in products in lower amounts (concentrations) to minimize irritation to the user, to maintain compatibility and stability with other components, and to facilitate low cost production. Preservative compositions may also be made available in concentrated form to later diluted in the manufacturing process.

Product pH may also be a consideration. Some preservative compounds have a narrow pH window for antimicrobial effects. As one example, many personal care products having pH ranges from about pH 5 to pH 9. Many preservative compounds exhibit no or low antimicrobial activity within this range.

Preservative compounds also differ in the breadth of their antimicrobial effects, with some compounds having very broad coverage against a wide variety of microorganisms, and other having activity against limited numbers and types of microorganisms. For example, one preservative compound may have activity against bacteria, while others have no antibacterial effect but exhibit anti-fungal or antiviral effects. As such, combinations or blends of traditional preservative compounds are very common.

Accordingly, selection of preservative compounds for any particular application is highly dependent on several factors or criteria, including the type of product, packaging design, anticipated uses, availability of antimicrobial efficacy data, spectrum of antimicrobial activity, types and amounts of other components in the product, product pH, potential for adverse or toxic effects in use or in production, compatibility problems and interactions with other components and costs. These considerations must be evaluated in formulating a product where preservatives are required or desirable. Predictability of results is difficult. What is effective in one product type may not be effective in another product type.

An important consideration in selecting antimicrobials is environmental safety and, ideally, freedom from irritating or toxic effects. Recent regulatory scrutiny of environmental and health and safety issues associated with the use of antimicrobials used as preservatives mandates that regulatory requirements be considered in using preservative compounds, whether used alone or in combination with other antimicrobial compounds. Formulators must therefore consider not only product requirements, but also regulatory requirements in coming up with an effective antimicrobial, preservative or biocidal composition for use in end use applications. As one example, formaldehyde or formaldehyde-donating preservative agents, such as ureas, or formaldehyde-releasing preservatives, such as quaternium compounds or hydantoins, while effective, may be prohibited in some countries. Similarly, amounts of certain preservative compounds utilized may be limited in certain end-use applications.

Safe antimicrobial, preservative and biocidal compounds are known in the art, which do not raise environmental or health and safety considerations. Unfortunately, many of these safer alternatives are only able to achieve antimicrobial activity at high concentrations that may be irritating. Even then, they may not be effective against all microbes, in particular spores. Traditional examples of antimicrobials generally deemed to be safe, particularly in personal care products, are sodium benzoate and benzyl alcohol used alone, or combined.

Sodium benzoate is a well-known antimicrobial preservative that is considered safe but may have limited antimicrobial activity when utilized alone. A disadvantage associated with the use of sodium benzoate is that it is not effective over a wide range of pH applications, thus limiting its use. Use of sodium benzoate in amounts of 0.01 wt. % to 2.0 wt. % is disclosed in combination with delta gluconolactone in U.S. Pat. No. 8,784,910 as an antimicrobial composition. Sodium benzoate is also reported as one component of a commercial liquid concentrate to preserve cosmetics, in combination with phenoxy ethanol and benzyl alcohol (wherein the phenoxy ethanol and benzyl alcohol are present in amounts greater than 25 wt. %). Other uses of sodium benzoate as an antimicrobial or preservative, alone or in combination with other antimicrobial preservative compounds, are known in the art.

Benzyl alcohol is an effective antimicrobial used in topically applied products but may require higher concentrations to achieve efficacy. As one example, benzyl alcohol is disclosed as a component of an improved preservative system for topical products, which also comprises disodium EDTA and a para-hydrobenzoic acid (paraben), in U.S. Pat. No. 6,120,758. Benzyl alcohol in combination with phenoxy ethanol and phenoxy propanol and glycerol ethers were found to be effective stabilizing compositions for cosmetic products. In addition, U.S. Pat. Nos. 7,537,776 and 8,501,206 disclose benzyl alcohol in combination with a sorbic acid salt or sodium benzoate and/or phenoxyethanol for use as a preservative concentrate for cosmetics. According to these patents, these active ingredients belong to "soft preservative active ingredients" meaning that they are effective only at relatively high use concentrations or may be improved by combination with other more effective active preservative ingredients.

In sum, while sodium benzoate and benzyl alcohol are effective and considered safe for use in some preparations, their use may be limited by a narrow spectrum of coverage, by pH ranges of products or by regulatory or industry limits on concentration levels that can be used in certain end-use applications. Combinations of sodium benzoate and benzyl alcohol with other components were found to be effective. however, combinations of sodium benzoate and benzyl alcohol with parabens and phenoxy ethanol and phenoxy propanol are now disfavored due to irritation and sensitivity when applied topically and other toxic effects. Hence, the amounts that may be utilized in products may be limited by regulation.

There remains, therefore, an ongoing need for safer alternative compounds to use in antimicrobial, preservative and biocidal applications that satisfy the considerations discussed above. In particular, there is a continuing need to develop antimicrobial compounds that have coverage against a wide range of organisms and that are compatible in low concentrations with a variety of components, effective across a range of pH, safe to handle and apply, within regulatory requirements or capable of satisfying regulatory requirements, and easily evaluated for efficacy. There is also a need to identify safe alternative compounds that may be used in combination with sodium benzoate and/or benzyl alcohol, or other organic acids or salts thereof and/or alcohols, to improve their antimicrobial effects across a broader spectrum of microorganisms and pH ranges.

The invention addresses many of the criteria considered in selecting an antimicrobial, preservative or biocidal compound for use in an end use application and is directed to compounds that satisfy the general criteria discussed above for many end use applications. Surprisingly, these compounds achieve unexpected antimicrobial efficacy at low levels (concentrations) and at a variety of pH ranges. In particular, it has been found that 3-phenyl propanol (3-PP) or 2-methyl-3-phenyl propanol (2M3PP), or mixtures thereof are highly effective antimicrobials when used alone, or in combination with other antimicrobial or preservative compounds, including without limitation organic acids (or salts thereof) and alcohols. In addition, it has also been found that 3-phenyl propanol and/or 2-methyl-3-phenyl propanol, or mixtures thereof, are highly effective as antimicrobials when combined with sodium benzoate and/or benzyl alcohol, although the invention is not limited to this specific combination. Unexpected antimicrobial efficacy has been demonstrated against a wide range of microorganisms and over typical pH ranges for a variety of products when using 3-phenyl propanol or 2-methyl-3-phenyl propanol, or mixtures thereof, alone or in combination with other antimicrobial compounds.

Both 3-phenyl propanol and 2-methyl-3-phenyl propanol are known flavor and/or fragrance or fragrance precursor components and solvents useful in a variety of products and manufacturing processes. 3-phenyl propanol, a naturally existing compound, and 2-methyl-3-phenyl propanol are environmentally safe and associated with few adverse effects. The use of 3-phenyl propanol and 2-methyl-3-phenyl propanol alone as effective antimicrobial agents has not been reported.

Uses of 3-phenyl propanol in combination with other compounds, including antimicrobials, has been reported, although not always for antimicrobial effects. As one example, WO 2016/084078 discloses blends of 3-phenyl propanol in amounts ranging from 2 up to 30 wt. % with an organic acid (selected from the group consisting of dehydroacetic acid (DHA), benzoic acid or mixtures thereof), a diol or triol (selected from the group consisting of a 1,2-diol 1,3-diol or mixtures thereof), and an emulsifier and/or alpha-dehydroxy acid, for use in personal care formulations.

As other examples, WO 2014/135650 discloses antimicrobial efficacy for blends of 3-phenyl propanol mixed with acetophenone; WO 2016 164555 discloses antimicrobial efficacy for blends of 3-phenyl propanol and propylene carbonate; WO 2015/090634 discloses antimicrobial efficacy for preservative blends comprising 3-phenyl propanol with ferulic acid ethyl ester preservative mixtures; WO 2014/191258 discloses antimicrobial efficacy for blends of 3-phenyl propanol with glyceryl ether preservative mixtures; WO 2014/009157 discloses antimicrobial efficacy for blends of 3-phenyl propanol with $C_1$ to $C_5$ diol preservative mixtures; WO 2007/071089 discloses antimicrobial efficacy for blends of 3-phenyl propanol with benzaldehyde preservative mixtures; EP 3023090 discloses antimicrobial efficacy for blends of 3-phenyl propanol with lactate ester preservative mixtures; EP 3332642, which discloses blends of 3-phenyl propanol with acetals and aldehydes for antibacterial perfuming compositions; WO 2017/116445 discloses blends of ionic tin, caprylyl glycol, and 3-phenyl propanol for oral care products. WO 2018/068825 discloses use of a certain ring compounds meeting the structural requirements of an identified "formula 1" as antimicrobial agents for personal care, household and nutrition products, wherein the compounds are selected from the group consisting of benzoic acid-3-hydroxypropyl ester, benzoic acid-3-hydroxyethyl ester, furoic acid-3-hydroxypropyl ester, furoic acid-3-hydroxyethyl ester, furoic acid methyl ester, anisic acid-3-hydroxypropyl ester, anisic acid-3-hydroxyethyl ester, N-methylsalicylamide, salicylamide, salicylic acid hydroxyethyl ester, salicylic acid hydroxypropyl ester, vanillic acid hydroxypropyl ester, and anthranilic acid hydroxypropyl ester. These compounds may be mixed with a variety of other compounds including benzoic acid (or salt hereof), or hydroxyl compounds, such as benzyl alcohol or 3-phenyl propanol.

3-phenyl propanol has also been used as an aryl alkanol solvent to prepare a solution of a separate microbiocidal compound for use in a polymer composition as described in U.S. Pat. Nos. 4,711,914 and 4,721,736.

None of the aforenoted patents and publications disclose the use of 3-phenyl propanol alone as an antimicrobial. Nor do any of them mention use of 2-methyl-3-phenyl propanol.

Many of the disclosed combinations using 3-phenyl propanol, while having some antimicrobial efficacy, may not achieve sufficient antimicrobial activity to pass accepted, standard preservative challenge testing as set forth by the United States Pharmacopeia and European Pharmacopeia, Important criteria for the evaluation and selection of an antimicrobial component are that its efficacy is easily determined. In addition, not all of the compositions may satisfy regulatory or industry standard-setting requirements for environmental safety or be free of adverse effects.

Use of 3-phenyl propanol or 2-methyl-3-phenyl propanol, or mixtures thereof, according to the invention, provides unexpected advantages when used with organic acids or salts thereof and/or alcohols, including without limitation unexpectedly improved microbial efficacy that satisfies stringent microbe challenge testing criteria for many end use applications, fewer regulatory or environmental concerns, and less adverse or toxic effects. A particularly advantageous combination is 3-phenyl propanol or 2-methyl-3-phenyl propanol, or mixtures thereof, in combination with sodium benzoate and/or benzyl alcohol.

The antimicrobial compositions of the invention are directed to use of 3-phenyl propanol or 2-methyl-3-phenyl propanol, or mixtures thereof, alone or in combination with organic acids (and salts thereof) and/or alcohols. While sodium benzoate and benzyl alcohol, alone or in combination, are preferred in combination with 3-phenyl propanol or 2-methyl-3-phenyl propanol, other organic acids (and salts thereof) and alcohols are within the scope of the invention.

The inventive antimicrobial compositions have applications for use in personal care products, cosmetics, toiletries, household products, and laundry products, detergents and cleaners. They are also useful antimicrobials for use in pharmaceutical compositions, healthcare products, medical products, veterinary products, and a variety of industrial products, such as paints, coatings, adhesives, caulks, sealants, inks, and plastisols and other polymeric dispersions and emulsions. The inventive antimicrobial compositions may be provided in low or high concentrations depending on their specific use.

It is an object of the invention to provide antimicrobial compounds for use in a variety of products based on use of 3-phenyl propanol or 2-methyl-3-phenyl propanol, alone or in combination with other compounds having antimicrobial activity, in particular organic acids or salts thereof and/or alcohols.

A further object of the invention is to provide preservative compositions for use in a wide variety of products comprising the antimicrobial compounds of the invention and blends thereof.

It is another object of the invention to provide a concentrated blend of antimicrobial compounds for use in end-use compositions.

Still another object of the invention is to provide household products, laundry products, detergents, cleaners, cosmetics, toiletries, or personal care products comprising the inventive antimicrobial compounds and blends thereof.

Yet another object of the invention is to provide antimicrobial compositions that are useful in pharmaceutical compositions, healthcare industry products, medical products, veterinary products, industrial products, paints, coatings, adhesives, sealants, caulks, inks, plastisols and other polymeric dispersions and emulsions, oil and gas recovery, and the like.

Other objects of the invention will be evident to one skilled in the art based on the disclosure herein.

SUMMARY OF THE INVENTION

The invention is directed to compositions having antimicrobial, preservative or biocidal activity against a wide range of microorganisms, including without limitation Gram positive and Gram negative bacteria, fungi, mold, yeast, protozoa and viruses, including spores. In particular, the invention is directed to compositions comprising 3-phenyl propanol or 2-methyl-3-phenyl propanol, or mixtures thereof, alone or in combination with other known antimicrobial compounds, including organic acids (or salts thereof) and/or alcohols, for use as in a variety of products and applications as antimicrobial, biocidal or preservative components. The invention is also directed to end-use products comprising the inventive compositions and methods of preserving personal care products, among others. Non-limiting embodiments of the invention are described below.

In one embodiment, the invention is directed to a composition having antimicrobial, biocidal, or preservative activity when used in an end use product or application, consisting of 3-phenyl propanol or 2-methyl-3-phenyl propanol or mixtures thereof, alone or in combination with an organic acid (or salt thereof) or an alcohol, or mixtures of an organic acid (or salt thereof) and an alcohol.

In a second embodiment, the invention is directed to an antimicrobial composition comprising 3-phenyl propanol or 2-methyl-3-phenyl propanol, or mixtures thereof, alone or in combination with an organic acid (or salt thereof) or an alcohol, or mixtures of an organic acid (or salt thereof) and an alcohol.

In another embodiment, the invention is directed to an antimicrobial composition comprising 3-phenyl propanol or 2-methyl-3-phenyl propanol, or mixtures thereof, in combination with sodium benzoate or benzyl alcohol, or mixtures of sodium benzoate and benzyl alcohol.

In yet another embodiment, the invention is directed to a synergistic tri-component composition consisting of a) 3-phenyl propanol or 2-methyl-3-phenyl propanol, or mixtures thereof, b) an organic acid (or salt thereof), and 3) an alcohol, wherein the tri-component antimicrobial composition achieves enhanced antimicrobial performance at a lower total wt. % loading than a dual component composition consisting of component (a) in combination with either an organic acid (or salt thereof) or an alcohol.

In still another embodiment, the invention is directed to a concentrated blend of antimicrobial compounds comprising 3-phenyl propanol, sodium benzoate and benzyl alcohol.

Another embodiment of the invention is a preservative comprising the inventive compositions.

An end-use embodiment is a skin lotion comprising 3-phenyl propanol, sodium benzoate and benzyl alcohol.

Other end-use embodiments include household products, disinfectants, cosmetics, personal care products, inks, industrial products, paints, coatings, adhesives, sealants, caulks, plastisols, polymeric dispersions, polymeric emulsions, pharmaceutical compositions, or oil and gas recovery and drilling processes containing or comprising: 3-phenyl propanol or 2-methyl-3-phenyl propanol, or mixtures thereof, alone, or in combination with organic acids (or salts thereof) and/or alcohols.

As another embodiment, the invention is a method of preserving a cosmetic or personal care product, comprising the step of adding the inventive antimicrobial compositions in amounts sufficient to achieve a two-day or 14-day, two-log reduction of at least one microorganism comprising *Pseudomonas aeruginosa, Staphylococcus aureus, Aspergillus brasiliensis, Candida albicans*, and *Escherichia coli*.

Other embodiments and uses for the inventive antimicrobial compositions will be evident to one skilled in the art based on the disclosure herein.

DETAILED DESCRIPTION OF THE INVENTION

The invention is directed to compositions having antimicrobial, biocidal or preservative properties against a wide range of microorganisms as described herein. In particular, the invention is directed to compositions comprising 3-phenyl propanol or 2-methyl-3-phenyl propanol, or mixtures thereof, used alone, or in combination with other antimicrobial compounds, in particular organic acids (or salts thereof) and/or alcohols for use as antimicrobial, biocidal or preservative components in a variety of end use products and applications. The invention is also directed to concentrated blends of antimicrobial compounds, at least one of which is 3-phenyl propanol, for later dilution in a variety of formulations, Finally, the invention is directed to products and applications for use of the inventive antimicrobial compositions.

For purposes of this invention, the terms "microorganisms", "microbiological organisms", "microbes" shall mean and include Gram positive and Gram negative bacteria, fungi, mold, fungi, yeast, protozoa and viruses, and spores thereof, and are used interchangeably.

"Antimicrobial" and "biocidal" shall mean and include the ability of the inventive antimicrobial compositions to destroy, deter, or render harmless, any harmful microorganism by chemical means. The terms "antimicrobial" and "biocidal" are used interchangeably herein. "Preservative" may also be used herein to describe the antimicrobial and biocidal effects of the inventive compositions, as well as to refer to an end use application for the compositions.

Concentrations of components may be expressed in parts per million "ppm" or weight percent "wt. %", "ppm" may be converted to weight percent by dividing the stated "ppm" by 10,000. The weight percent is based upon the total weight of all components in an end use composition, unless otherwise stated.

Essential components of the present invention are 3-phenyl propanol and structurally similar 2-methyl-3-phenyl propanol, compounds having known flavor and/or fragrance properties and reported antimicrobial effects when combined with acetophenones, aromatic alcohols, diols and triols, as discussed more fully above.

The present invention is based upon the discovery that 3-phenyl propanol and 2-methyl-3-phenyl propanol, or mixtures thereof, alone, or when combined with other known antimicrobial compounds, achieve unexpected activity against a broad spectrum of Gram positive bacteria, Gram negative bacteria, fungi, mold, yeast, protozoa and virus microorganisms, including spores, even when used at lower than previously reported levels. In combination with other known antimicrobial compounds, an unexpected synergism has been discovered allowing for use of a lower antimicrobial load than that utilized for any of the antimicrobial compounds alone.

Figure 26:
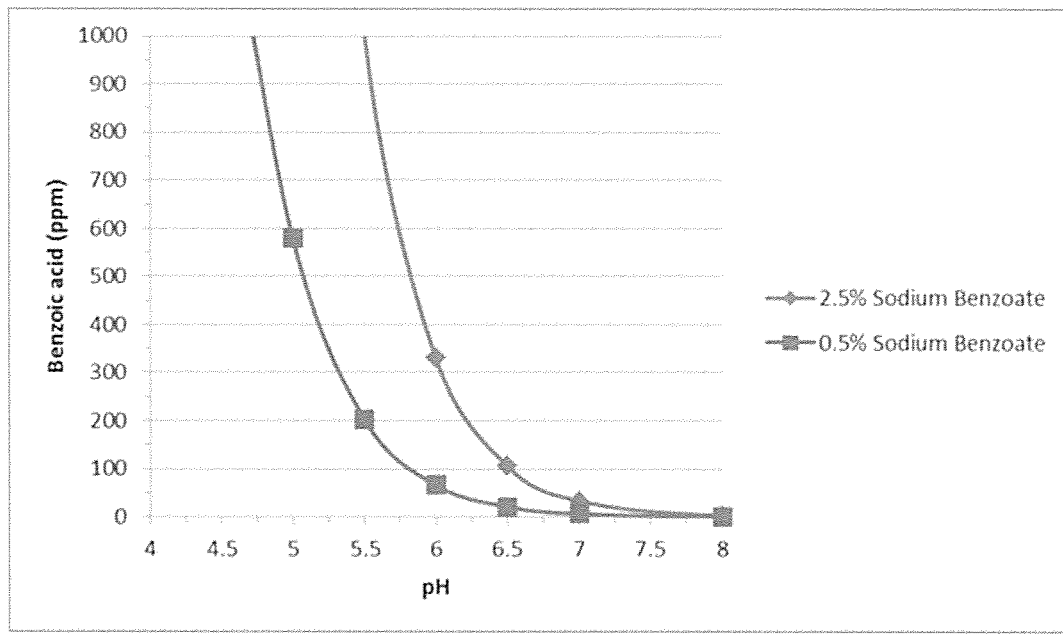
FIG. 26 reflects a chart showing the effect of sodium benzoate loaded into a product at 2.5 wt. %. The active species, benzoic acid, increases as pH decreases.

Suitable compounds for use in combination with 3-phenyl propanol and 2-methyl-3-phenyl propanol, or mixtures thereof, include organic acids or salts thereof and alcohols, including without limitation sodium benzoate and benzyl alcohol. Both sodium benzoate and benzyl alcohol, alone and in combination with each other, are used as preservative compounds in a variety of applications. Benzoic acid has been shown in scientific literature to be the active antimicrobial species over sodium benzoate. However, there exists an equilibrium balance between sodium benzoate and benzoic acid based on benzoic acid's pKa of 4.2. By way of explanation, if sodium benzoate is loaded into a product at 2.5 wt. %, the concentration of benzoic acid increases as pH decreases as shown in FIG. 26. The antimicrobial efficacy of sodium benzoate generally diminishes at higher pH due because of the loss of benzoic acid concentration, due to the pKa and pH dependence thereon.

There are limitations on the use of sodium benzoate and benzyl alcohol. In particular, their antimicrobial efficacy may be limited by pH of the end use composition, concentration and type of other components, compatibilities, and concentration limits or amounts required to be effective against specific microbes or in specific applications, or governmental or industry regulations or industry practice standards that are specific to some applications.

Other organic acids (or salts thereof) and alcohols are useful in combination with 3-phenyl propanol or 2-methyl-3-phenyl propanol. Exemplary non-limiting organic acids (and salts thereof) include: benzoic acid, dehydroacetic acid, acetic acid, citric acid, formic acid, propionic acid, fumaric acid, sorbic acid, lactic acid, sodium benzoate, potassium benzoate, potassium sorbate, sodium sorbate, sodium citrate, or sodium lactate, or mixtures thereof. Exemplary non-limiting alcohols include: ethanol, propanol, benzyl alcohol, 2,4 dichlorobenzyl alcohol, benzyl ethanol, phenyl ethanol or phenoxyethanol, or mixtures thereof. Other organic acids and salts thereof and alcohols useful in the inventive compositions will be evident to one skilled in the art.

Amounts of 3-phenyl propanol or 2-methyl-3-phenyl propanol, or mixtures thereof, useful to achieve antimicrobial effects when used in an end-use formulation range from 0.005 wt. % to 1.99 wt. %, preferably 0.01 wt. % to 1.99 wt. %, more preferably 0.1 wt. % to 1.99 wt. %, based upon the total weight of the components of the end use product, Surprisingly, these amounts achieve antimicrobial efficacy in use despite being at a lower concentration than that typically used to achieve antimicrobial or biocidal effects in, or preservation of, in end use products and applications.

In particular end use applications, amounts of 2-methyl-3-phenyl propanol may be used in amounts ranging from 0.01 wt. % to 5 wt. %. As a non-limiting example, an antimicrobial composition consisting of 2-methyl-3-phenyl propanol ranging from 0.01 wt. % to 5 wt. % is useful as an antimicrobial agent for cosmetics, coatings, household products and various other applications.

Amounts of the inventive compositions used in end use applications may also vary depending on the number of components in a combination. As one example, a synergistic tri-component antimicrobial composition, consisting of 3-phenyl propanol or 2-methyl-3-phenyl propanol, or mixtures thereof, in combination with both an organic acid or salt thereof and an alcohol is expected to achieve enhanced antimicrobial performance at a lower total wt. % loading (in an end use application) than a dual component mixture consisting of the 3-phenyl propanol or 2-methyl-3-phenyl propanol in combination with either, but not both, of an organic acid or salt thereof or an alcohol.

Amounts of sodium benzoate suitable for use in combination with 3-phenyl propanol or 2-methyl-3-phenyl propanol range from 0.005 wt. % to 10 wt. %, and amounts of benzyl alcohol range from 0.005 wt. % to 10 wt. %, based upon the total weight of the components of the end use product. Suitable amounts of each component may vary within the stated ranges based upon end use applications, concentration and type of other components, compatibilities, interactions, pH considerations, regulations and industry standards, and the like.

Ranges for other organic acids (or salts thereof) and other alcohols in combination with 3-phenyl propanol or 2-methyl-3-phenyl propanol are expected to be the same or substantially close to the ranges for sodium benzoate and benzyl alcohol.

As described above, embodiments of the invention include use of 0.01 to 1.99 wt. % 3-phenyl propanol or 2-methyl-3-phenyl propanol, or mixtures thereof, as an antimicrobial, biocide or preservative in an end use formulation. A particularly preferred end-use includes use of 0.01 to 1.99 wt. % 3-phenyl propanol or 2-methyl-3-phenyl propanol, or mixtures thereof, as an antimicrobial agent in a skin lotion product. In another preferred end-use, 0.35 wt. %

3-phenyl propanol or 2-methyl-3-phenyl propanol, or mixtures thereof, is used in combination with sodium benzoate and benzyl alcohol, both present in amounts of 0.25 wt. % in a skin lotion composition.

It has been demonstrated herein that both 3-phenyl propanol and 2-methyl-3-phenyl propanol are effective antimicrobials across a wide range of pH encountered in a variety of products. Given their structural similarity, 3-phenyl propanol and 2-methyl-3-phenyl propanol may also be combined and utilized in the same total concentration ranges as that described for individual use.

The antimicrobial compositions of the invention may also be provided in concentrated form for ease of handling and costs. Concentrated forms are particularly useful in the manufacturing process, where they can be later diluted with water or other solvents. Concentrated blends of the antimicrobial components comprise: 3-phenyl propanol or 2-methyl-3-phenyl propanol, or mixtures thereof, in amounts ranging from 30.2 wt. % to 99.5 wt. %, alone, or in combination with an organic acid (or its salt) and an alcohol, wherein the organic acid or salt thereof is present in amounts of ranging from about 0.25 wt. % to about 39.9 wt. % and the alcohol is present in amounts ranging from about 0.25 wt. % to about 39.9 wt. %, based on the total weight of the concentrated blend. A particularly preferred embodiment is a concentrated antimicrobial blend comprising 41 wt. % of 3-phenyl propanol or 2-methyl-3-phenyl propanol, or mixtures thereof, 29.5 wt. % sodium benzoate, and 29.5 wt. % benzyl alcohol. Another preferred embodiment is a concentrated antimicrobial blend comprising 3-phenyl propanol or 2-methyl-3-phenyl propanol, or mixtures thereof, present in amounts ranging from 30.1 wt. % to 99 wt. %, in combination with an organic acid (or salt thereof) and an alcohol, wherein the organic acid (or salt thereof) and alcohol are added in amounts sufficient to add up to 100 wt. %, based on the weight of the concentrated antimicrobial blend.

Non-limiting examples of solvents that may be used to dilute the inventive compositions include water, ethanol, propanol, isopropyl alcohol, propylene glycol, dipropylene glycol, diethylene glycol dibenzoate, dipropylene glycol dibenzoate, propylene glycol dibenzoate, 3-phenyl propyl benzoate, acetone, ethyl acetate, n-butyl acetate, propylene glycol n-butyl ether, dipropylene glycol n-butyl ether, diethylene glycol monomethyl ether, diethylene glycol monoethyl ether, dipropylene glycol dimethyl ether, xylene, toluene, tetrahydrofuran, chloroform, methyl ethyl ketone, cyclohexane or mixtures thereof. Other solvents useful with the inventive antimicrobial compositions or the particular end use applications utilizing them will be known to one skilled in the art.

Antimicrobial compositions of the invention may have their performance boosted or enhanced by the addition of other "boosting" compounds. Non-limiting examples of such compounds include: chelating agents, such as ethylenediamine tetraacetic acid or the sodium salt thereof (EDTA), sodium gluconate, glycols, such as caprylyl glycol, and GLDA-Na$_4$ (glutamic acid N,N-diacetic acid, tetrasodium salt).

The inventive antimicrobial compositions are described with respect to efficacy in tryptic soy broth, which is an excellent surrogate for evaluating antimicrobial efficacy in water-based or aqueous applications. End use applications for the inventive antimicrobial compositions are described with respect to use in skin lotion formulations, a waterborne coating, laundry detergent and a household cleaner; however, the invention is not intended to be limited as such. As demonstrated herein, the antimicrobial compositions of the invention have efficacy over a range of pH (~3.0 to ~10). End-use applications for the inventive antimicrobial compositions include without limitation household products, laundry products, detergents, cleaners, cosmetics, toiletries, personal care compositions, healthcare products, medical products, veterinary products and industrial products and processes. Non-limiting examples of industrial end-use applications include paint, coatings, lacquers, inks, adhesives, caulks, sealants, plastisols and other polymeric dispersions and emulsions, oil and gas recovery and drilling processes. As demonstrated in the examples, the antimicrobial compositions of the invention have particular utility in any aqueous-based formulations, both water soluble or those utilizing water as a carrier. Still other end-use applications will be evident to one skilled in the art.

The invention is illustrated in the examples set forth below.

EXAMPLES

Methodology and Materials

Challenge Testing Methodology—Experimental—

Several industry standard testing methodologies exist for evaluating antimicrobial efficacy through microbe challenge testing. Two common examples of such standards include United States Pharmacopeia Chapter 51 (USP 51) and European Pharmacopeia Chapter 7 (EP) testing methodology, although the invention is not limited to use of these two standards. One skilled in the art would be able to determine and utilize other industry testing methods useful to evaluate the efficacy of the present inventive compositions. The USP 51 and EP exemplary methodologies are particularly useful in that they have criteria and methodologies distinguishing between oral products, topical products and pharmaceutical products, among others.

In conducting the testing, the product is separated out into individual containers, each being challenged with one of the method-specified microorganisms (*S. aureus*—ATCC 6538 USP51/EP, *E. coli*—ATCC 8739 USP 51, *P. aeruginosa*—ATCC 9027 USP51/EP, *C. albicans*—ATCC 10231 USP51/EP, and *A. brasiliensis*—ATCC 16404 USP51/EP) at a concentration of >1×10$^5$ CFU/g or ml. The initial concentration of each microorganism is determined by inoculating a control substance and using standard dilution and plating techniques. At the time of test initiation, a separate volume, typically 1 ml or 1 g, of the product is diluted in a volume of chemical neutralizer broth, to be used in the neutralization and recovery validation. The inoculated product is held at room temperature and is evaluated at specific intervals. USP-51 evaluates at the 14-day and 28-day intervals. EP testing evaluates results at the 2-day, 7-day, 14-day, and 28-day marks. At each contact time, the inoculated product is chemically neutralized and plated using standard dilution and plating techniques. After a period of incubation (48 hours for bacteria, up to 5 days for yeast and mold) surviving microorganisms are counted, and the log reduction of each microorganism at each interval is reported.

For the European Pharmacopeia, a "pass" test for efficacy is a two-log reduction for bacteria after two days, three-log reduction for bacteria after three days, two-log reduction for mold and yeast at 14 days and no increase at 28 days. For the USP-51, a two-log reduction in bacteria is required at 14 days and no increase at 28 days. For mold and yeast, USP-51 requires no increase at 14 days and 28 days. "No increase" is defined as a 0.5 log reduction.

Tryptic soy broth, commonly referred to as soybean-casein digest medium or tryptic soy broth, is used as a growth medium to cultivate a wide variety of microorganisms. Tryptic soy broth is an exceptionally difficult environment to preserve as it is an ideal growth medium for microbes with optimized levels of water and nutrients. As such, it is an exceptional test medium and surrogate for evaluating antimicrobial efficacy, particularly for water-based or aqueous applications, although its value is not limited as such. The tryptic soy broth formula per liter is listed in the table below.

| Formula per Liter | |
|---|---|
| Casein Digest peptone | 17.0 g |
| Papaic Digest of Soybean Meal | 3.0 g |
| Dipotassium Phosphate | 2.5 g |
| Sodium Chloride | 5.0 g |
| Dextrose | 2.5 g |

Skin Lotion Formulation Experimental—An exemplary, model skin lotion having a pH of 6.5 as set forth below in Table 1 was prepared for testing. The invention is not limited to use in this specific lotion but was used to illustrate the advantages of the invention.

TABLE 1

| Skin Lotion Formulation | | |
|---|---|---|
| INCI Name | Wt. % | Function |
| Stage A | | |
| Water | Varies | Carrier |
| Glycerin | 5.0% | Humectant |
| Xantham Gum | 0.1% | Rheology Modifier |
| Stage B | | |
| Cetearyl Alcohol | 3.0% | Rheology Modifier |
| Steareth-21 | 2.0% | Emulsifier |
| Steareth~2 | 2.0% | Emulsifier |
| Mineral Oil | 5.0% | Emollient |
| Petrolatum | 2.0% | Emollient |
| Stage C | | |
| Sodium Benzoate | Varies | Preservative |
| Benzyl Alcohol | Varies | Preservative |
| 3-Phenylpropanol | Varies | Antimicrobial |

All of the microbial challenge testing was conducted by a Food and Drug Administration (FDA) certified outside testing lab utilizing standard USP-51 and European Pharmacopeia methodologies as discussed above. Antimicrobial efficacy was determined in tryptic soy broth growth media, pH-balanced with sodium hydroxide or hydrochloric acid as required for specific pH ranges. Product use applications involve a variety of pH conditions. As such, efforts were made to assess efficacy over a typical range of pH conditions. In addition, antimicrobial compositions were added in amounts reflecting the wt. % used in an end use product, based on the total weight of all of the components of the end use product.

Example 1—Tryptic Soy Broth Studies at pH 6.5

The efficacy of 3-phenyl propanol in tryptic soy broth growth media at pH 6.5 versus a number of microbes was evaluated according to methods described in the Challenge Testing Methodology section, above.

The data shown in FIGS. 1 through 5 show the antimicrobial performance of various concentrations of 3-phenyl propanol (in wt. %) against the selected microbes (*A. brasiliensis, C. albicans, E. coil, P. aeruginosa,* and *S. aureus*) at 30 minutes, two days, seven days, fourteen days and twenty-eight days.

The data reflect that 3-phenyl propanol was efficacious versus bacteria, yeast and mold. According to EP criteria described in the Challenge Testing Methodology section above, 3-phenyl propanol achieved passing efficacy at 1 wt. %. According to USP-51 criteria in the Challenge Testing Methodology section above, 3-phenyl propanol achieved passing efficacy at 0.5 wt. %.

The data demonstrates that 3-phenyl propanol alone achieved significant log reduction against a variety of organisms at pH 6.5. As discussed, tryptic soy broth is an exceptionally difficult environment to preserve as it is an ideal growth medium for microbes with optimized levels of water and nutrients. The performance demonstrated that 3-phenyl propanol can preserve aqueous-based applications.

Example 2—Tryptic Soy Broth Studies at pH 8.0

The efficacy of 3-phenyl propanol in tryptic soy broth growth media at pH 8.0 versus a number of microbes was evaluated according to methods described in the Challenge Testing Methodology section above.

The data shown in FIGS. 6 through 10 show the antimicrobial performance of various concentrations of 3-phenyl propanol (in wt. %) against the selected microbes (as used in Example 1) at 30 minutes, two days, seven days, fourteen days and twenty-eight days.

The data reflect that 3-phenyl propanol was efficacious versus bacteria, yeast and mold. According to EP criteria described in the Challenge Testing Methodology section above, 3-phenyl propanol achieved passing efficacy at 1 wt. %. According to USP-51 criteria described in the Challenge Testing Methodology section, 3-phenyl propanol achieved passing efficacy at 0.25 wt. %.

The data demonstrates that 3-phenyl propanol alone achieved significant log reduction against a variety of organisms at pH 8.0. The performance demonstrated that 3-phenyl propanol can preserve aqueous based applications in a variety of pH conditions.

Example 3—Tryptic Soy Broth Studies at pH 9.0

Figure 1:
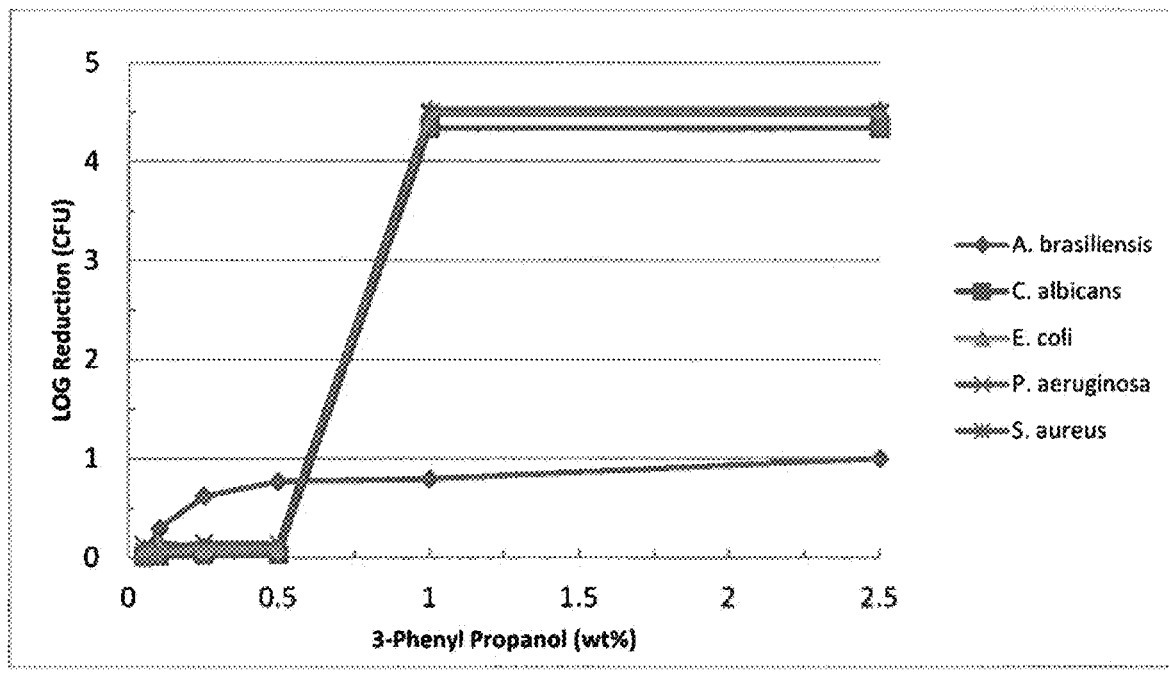
FIG. 1 reflects log reduction data for colony forming units (CFU) of microbe strains exposed to 3-phenyl propanol at various concentrations in tryptic soy broth growth media at pH 6.5 after 30 minutes.
Figure 2:
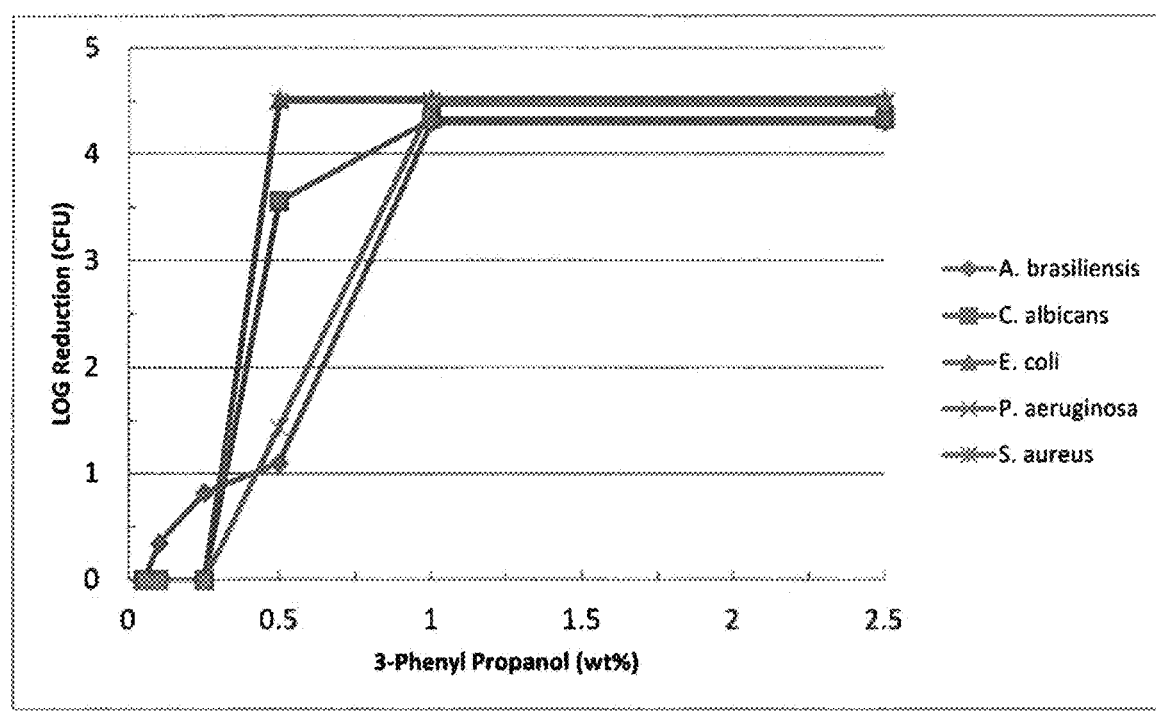
FIG. 2 reflects log reduction data for colony forming units (CFU) of microbe strains exposed to 3-phenyl propanol at various concentrations in tryptic soy broth growth media at pH 6.5 after two days.
Figure 3:
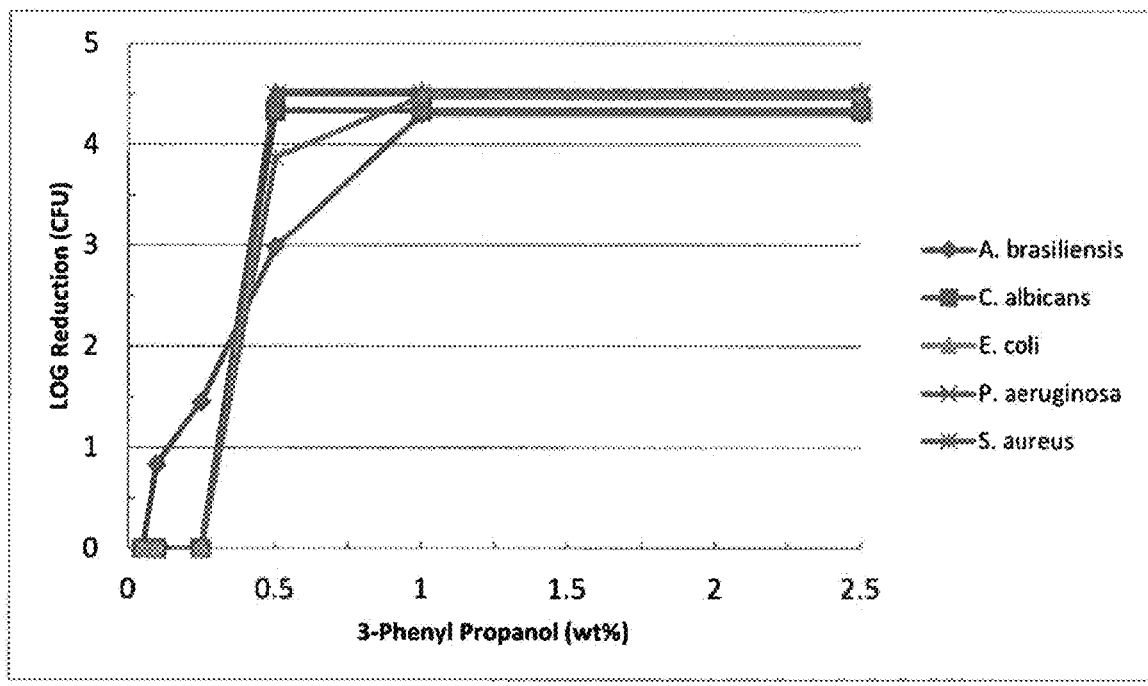
FIG. 3 reflects log reduction data for colony forming units (CFU) of microbe strains exposed to 3-phenyl propanol at various concentrations in tryptic soy broth growth media at pH 6.5 after seven days.
Figure 4:
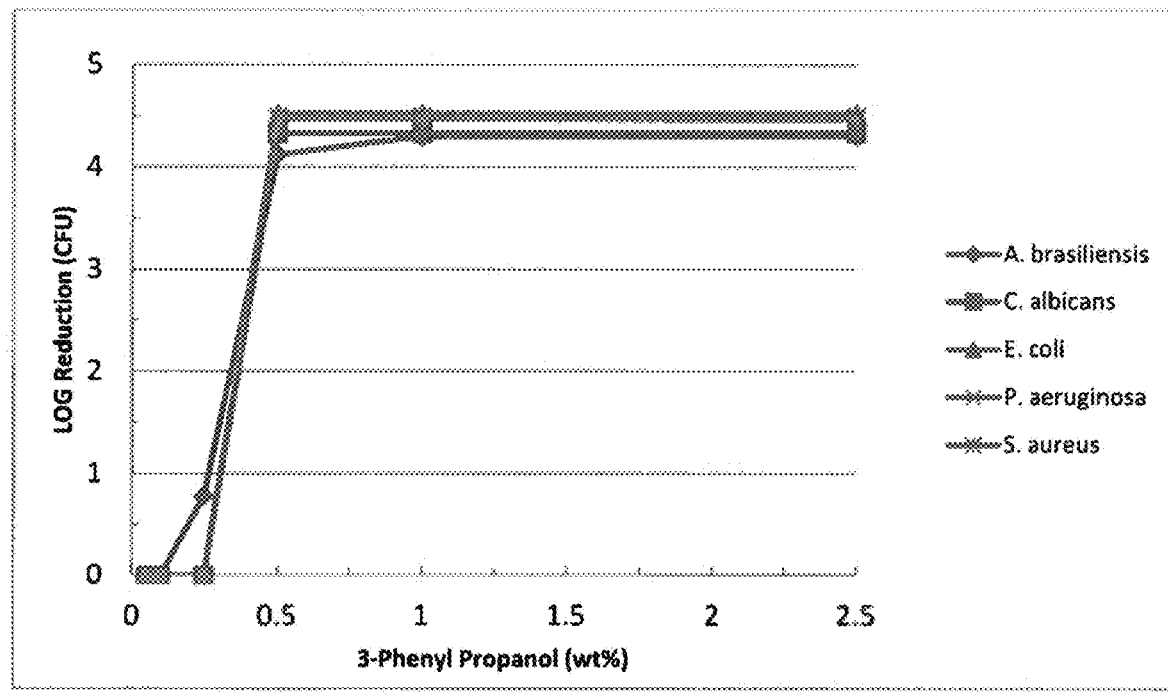
FIG. 4 reflects log reduction data for colony forming units (CFU) of microbe strains exposed to 3-phenyl propanol at various concentrations in tryptic soy broth growth media at pH 6.5 after fourteen days.
Figure 5:
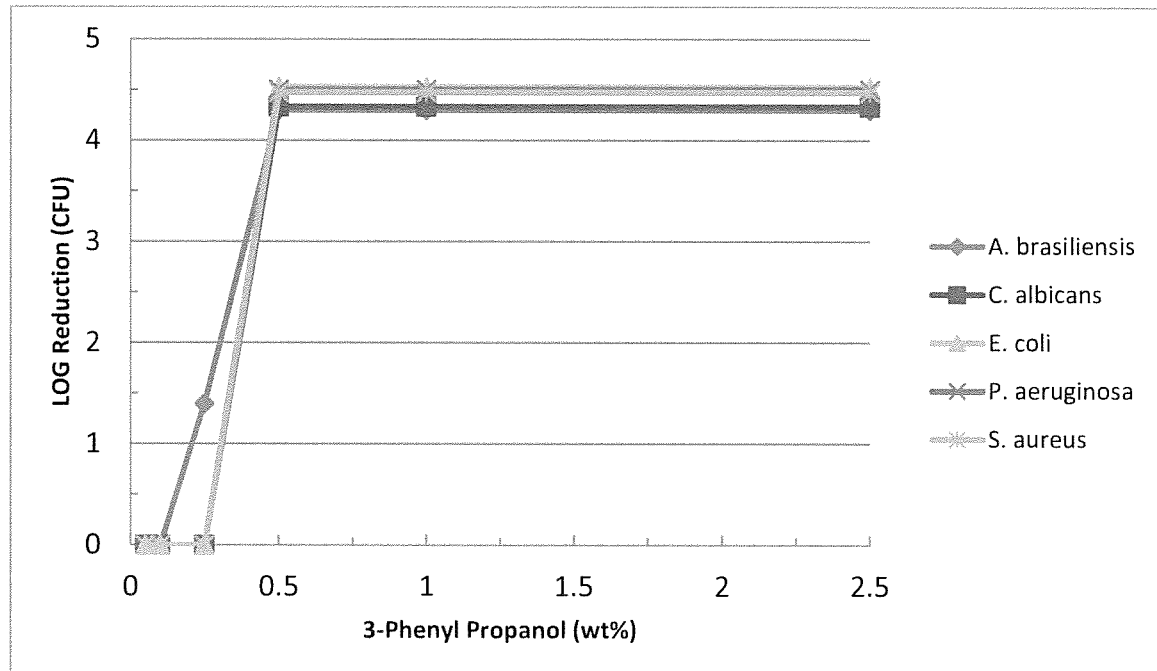
FIG. 5 reflects log reduction data for colony forming units (CFU) of microbe strains exposed to 3-phenyl propanol at various concentrations in tryptic soy broth growth media at pH 6.5 after twenty-eight days.
Figure 6:
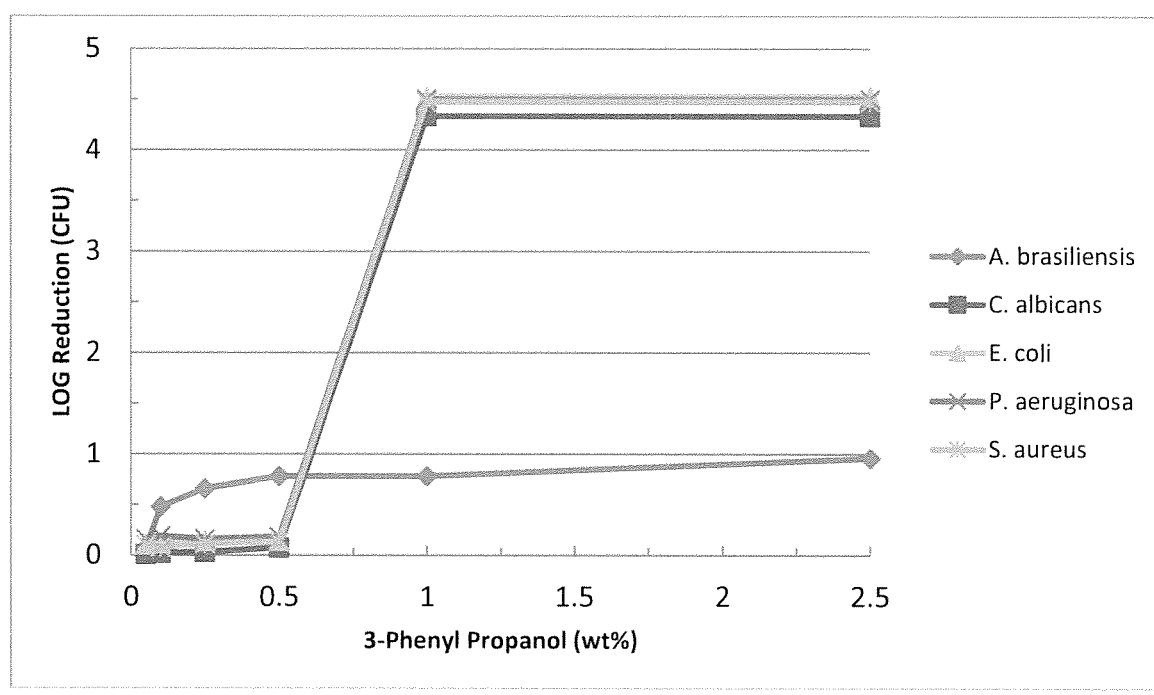
FIG. 6 reflects log reduction data for colony forming units (CFU) of microbe strains exposed to 3-phenyl propanol at various concentrations in tryptic soy broth growth media at pH 8.0 after 30 minutes.
Figure 7:
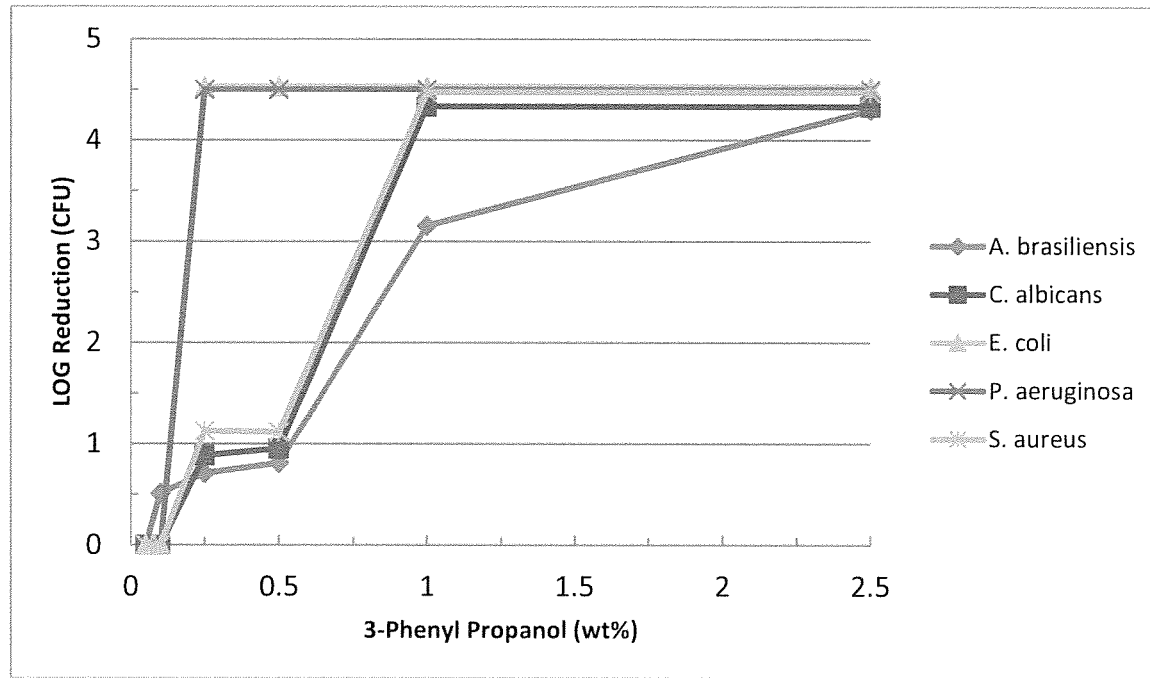
FIG. 7 reflects log reduction data for colony forming units (CFU) of microbe strains exposed to 3-phenyl propanol at various concentrations in tryptic soy broth growth media at pH 8.0 after two days.
Figure 8:
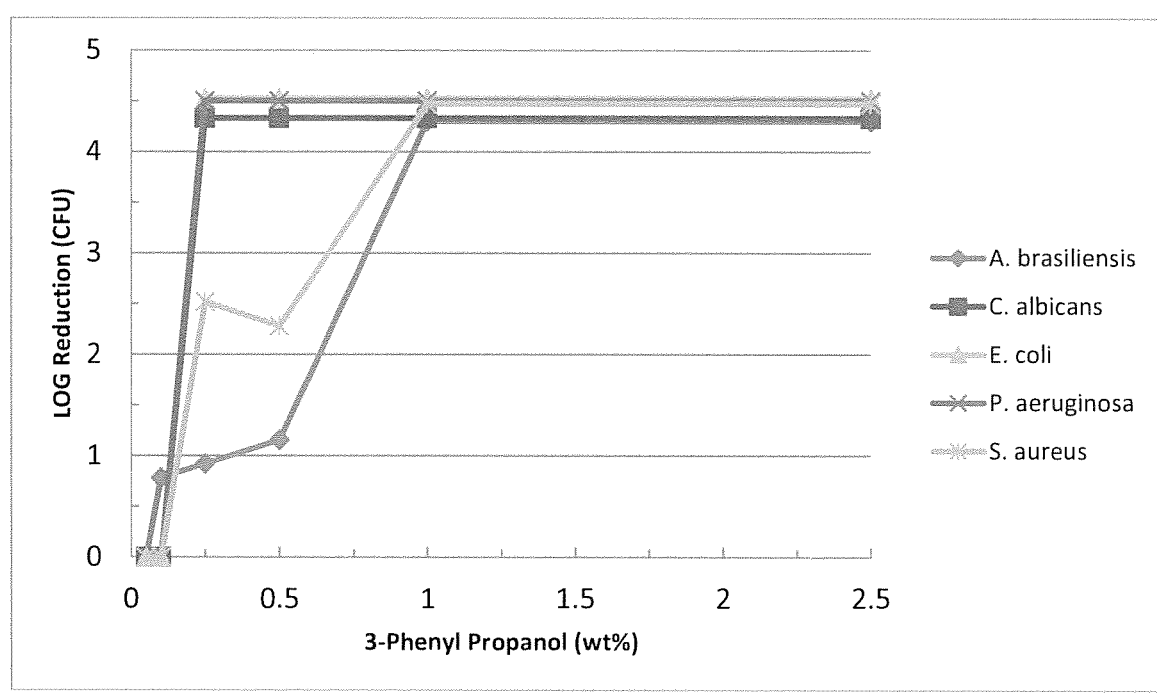
FIG. 8 reflects log reduction data for colony forming units (CFU) of microbe strains exposed to 3-phenyl propanol at various concentrations in tryptic soy broth growth media at pH 8.0 after seven days.
Figure 9:
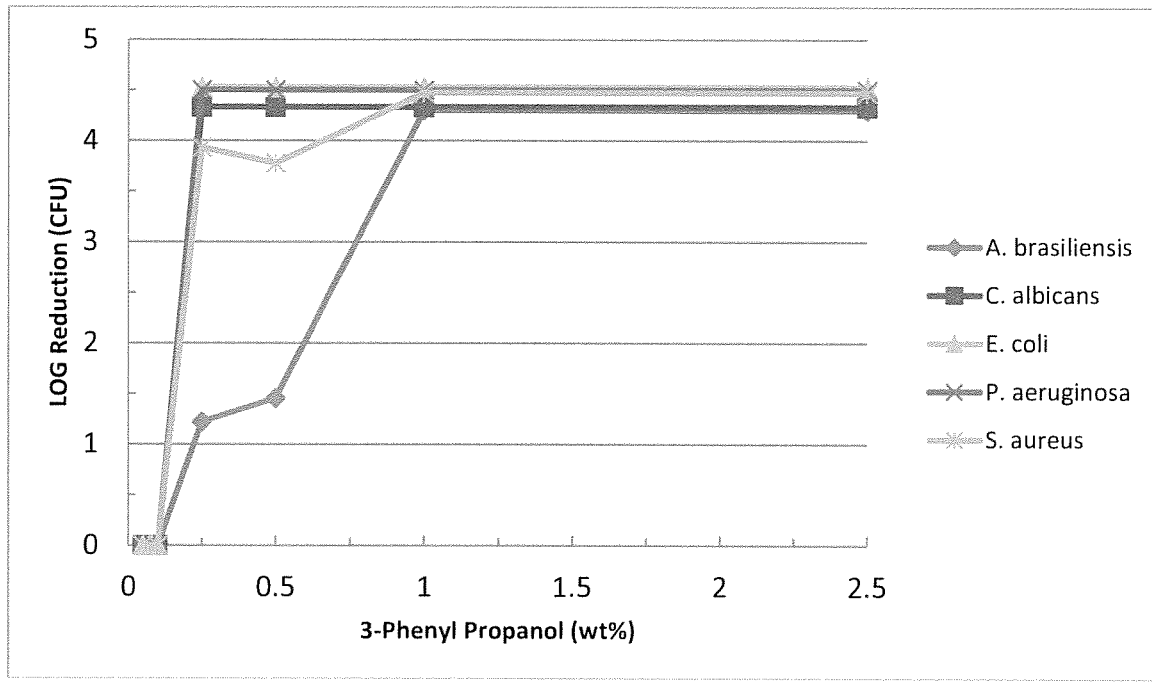
FIG. 9 reflects log reduction data for colony forming units (CFU) of microbe strains exposed to 3-phenyl propanol at various concentrations in tryptic soy broth growth media at pH 8.0 after fourteen days.
Figure 10:
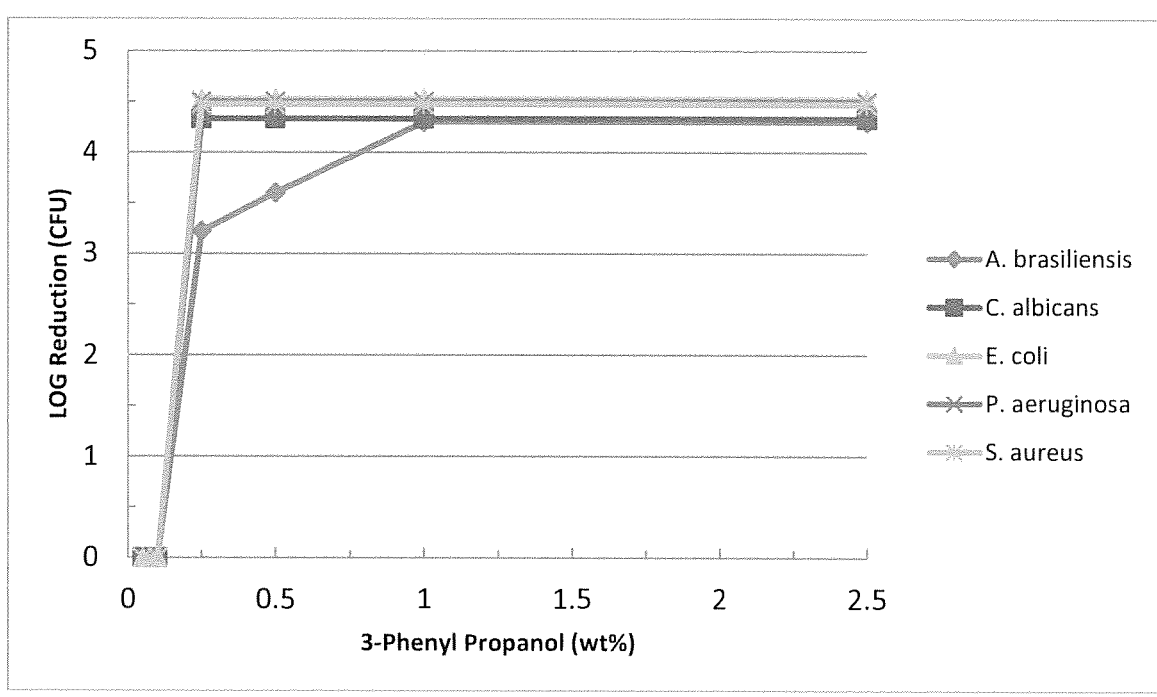
FIG. 10 reflects log reduction data for colony forming units (CFU) of microbe strains exposed to 3-phenyl propanol at various concentrations in tryptic soy broth growth media at pH 8.0 after twenty-eight days.
Figure 11:
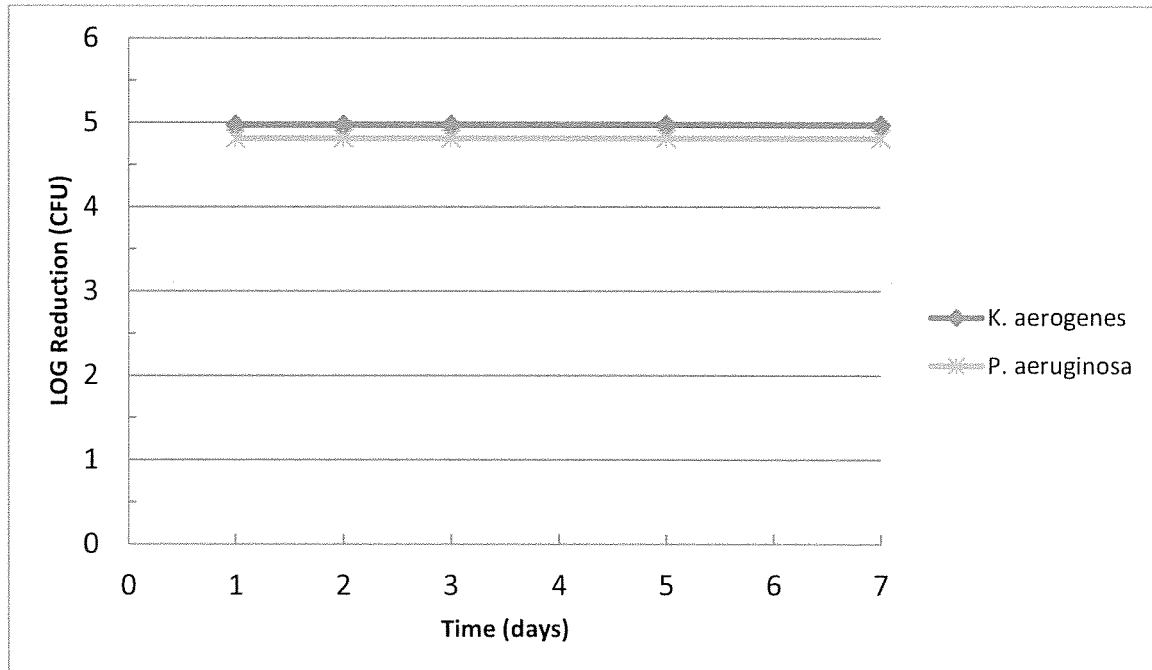
FIG. 11 reflects log reduction data for colony forming units (CFU) of microbe strains exposed to benzyl alcohol at 2.5 wt. % in tryptic soy broth at pH 9.0 up to one week.
Figure 12:
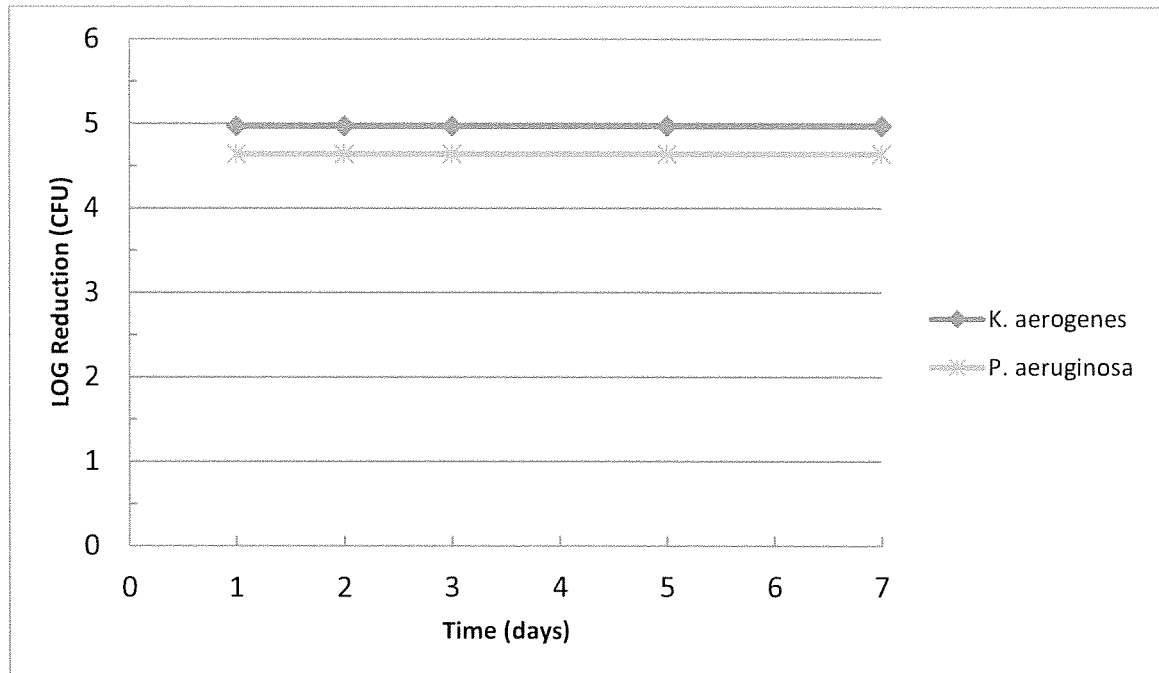
FIG. 12 reflects log reduction data for colony forming units (CFU) of microbe strains exposed to 2-methyl-3-phenyl propanol at 0.5 wt. % in tryptic soy broth at pH 9.0 up to one week.

FIGS. 11 and 12 show unexpected antimicrobial effectiveness over time achieved by benzyl alcohol (2.5 wt. %) and 2-methyl-3-phenyl propanol (0.5 wt. %), respectively, at pH 9 in tryptic soy broth. Strains of *K. aerogenes* (ATCC 13048) and *P. aeruginosa* (ATCC 9027) were utilized for this testing as they are commonly found in many products, including without limitation cosmetics and coatings. These organisms were challenged in the soy broth using the same methods described in the Challenge Testing Methodology section. The time points were selected from ASTM 2574, which is a method for evaluating antimicrobial efficacy in waterborne emulsion based paints.

Figure 13:
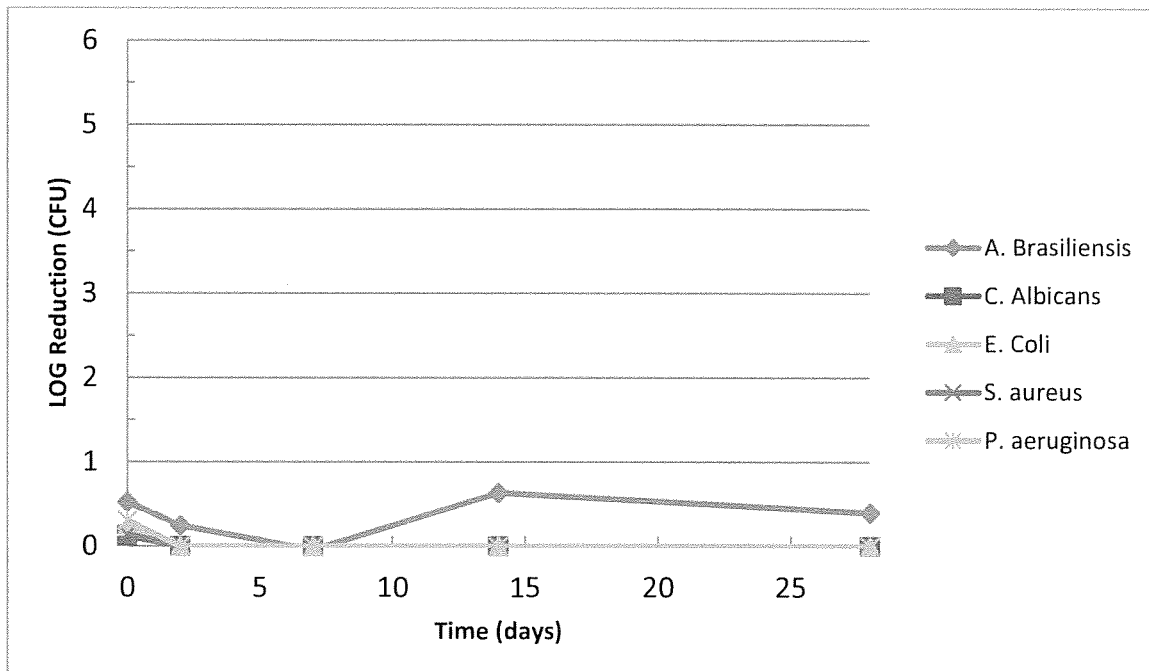
FIG. 13 reflects log reduction data for colony forming units (CFU) of microbe strains in tryptic soy broth growth media at pH 9.0 up to 28 days without an antimicrobial present.

FIG. 13 shows the response of microbe strains (as in Example 1) in tryptic soy broth at pH 9 without an antimicrobial present. The microbes either grow or are not controlled sufficiently for water-based application products, despite a higher pH.

Example 5—Tryptic Soy Broth Studies at pH 3.0

Figure 14:
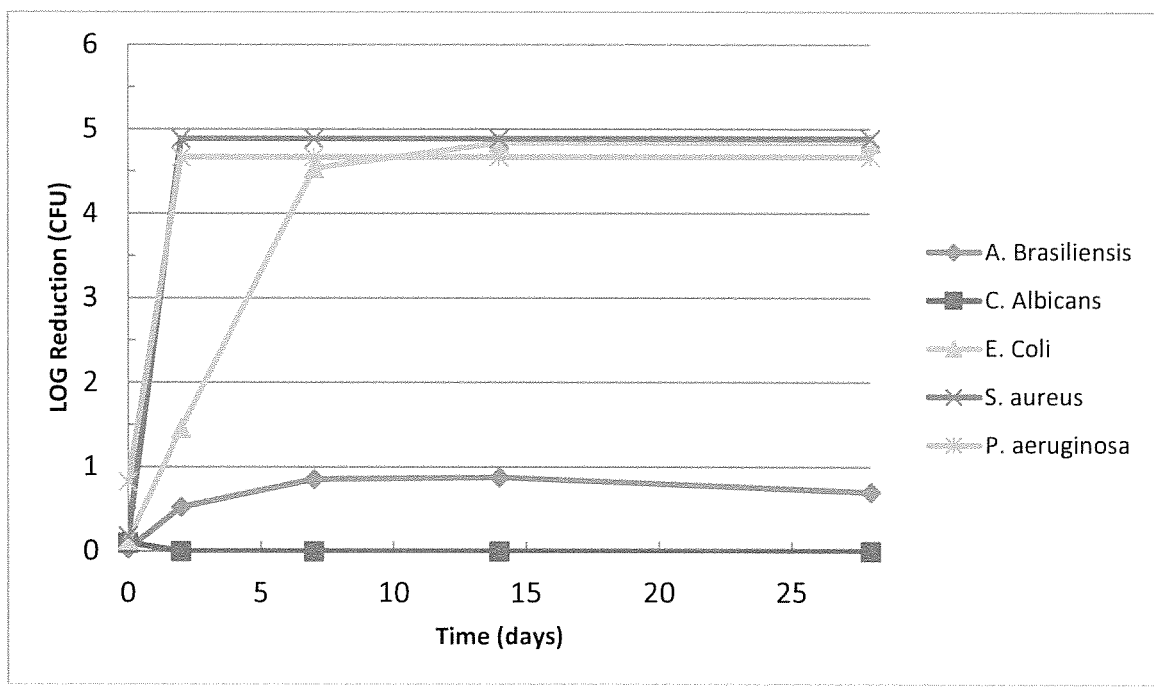
FIG. 14 reflects log reduction data for colony forming units (CFU) of microbe strains in tryptic soy broth growth media at pH 3.0 up to 28 days.
Figure 15:
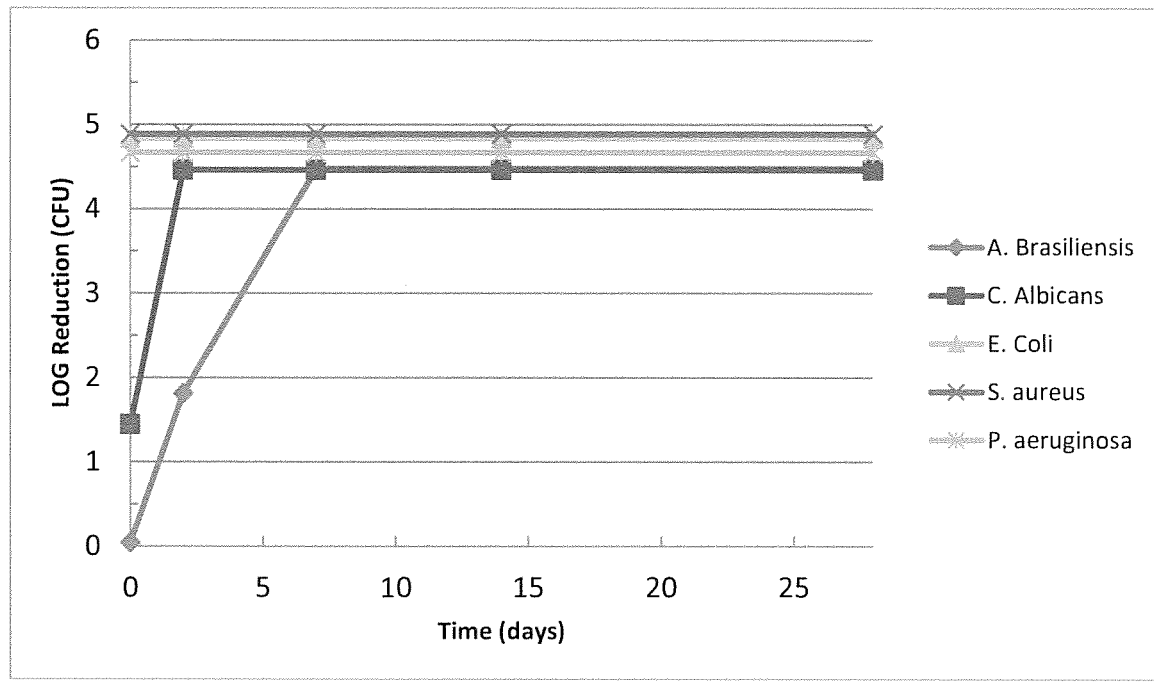
FIG. 15 reflects log reduction data for colony forming units (CFU) of microbe strains exposed to 0.5 wt. % 3-phenyl propanol in tryptic soy broth growth media at pH 3.0 up to 28 days.

FIG. 14 (control, no antimicrobial) and FIG. 15 demonstrated the effectiveness of 3-phenyl propanol at 0.5 wt. % against microbe strains (as in Example 1) at pH 3 in tryptic soy broth growth media when compared to the same microbes without an antimicrobial present. While the acidic pH of the control showed some log reduction for some microbes tested, neither the spore-producing fungus (*A. brasiliensis*) or the yeast (*C. albicans*) responded to the lower pH.

Example 6—Tryptic Soy Broth Studies at pH 10

Figure 16:
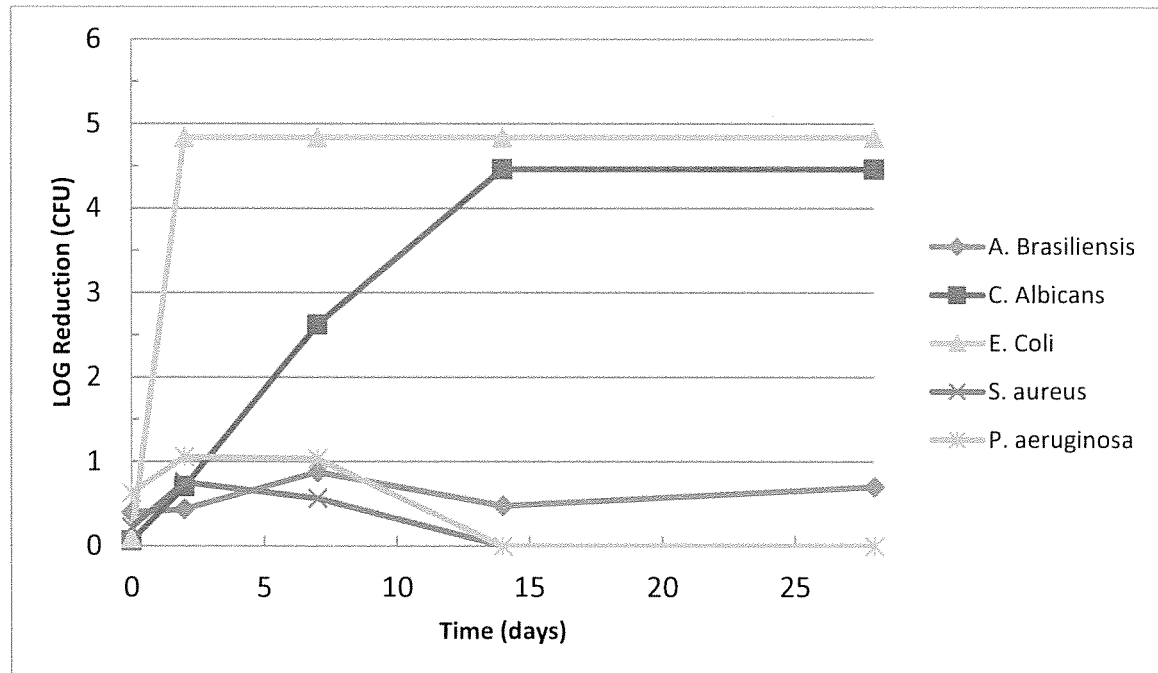
FIG. 16 reflects log reduction data for colony forming units (CFU) of microbe strains in tryptic soy broth growth media at pH 10 up to 28 days.
Figure 17:
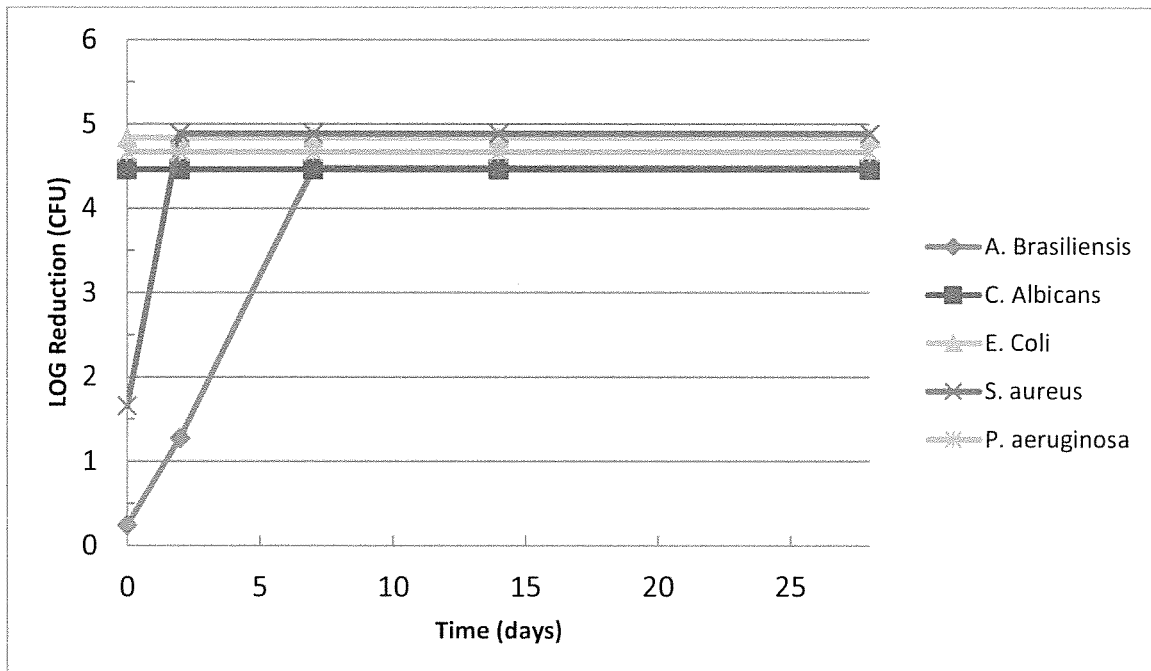
FIG. 17 reflects log reduction data for colony forming units (CFU) of microbe strains exposed to 0.5 wt. % 3-phenyl propanol in tryptic soy broth growth media at pH 10, FIG. 18 reflects log reduction data for colony forming units (CFU) of microbe strains exposed to 3-phenyl propanol at various concentrations in skin lotion media at pH 6.5 after two days, each skin lotion formation having a fixed concentration of 0.25 wt. % of sodium benzoate and 0.25 wt. % of benzyl alcohol.

FIG. 16 (control, no antimicrobial) and FIG. 17 demonstrated the effectiveness of 3-phenyl propanol at 0.5 wt. % against microbe strains (as in Example 1) at pH 10 in tryptic soy broth growth media when compared to the same microbes without an antimicrobial present. While the higher, alkaline pH had an effect on *E. coli* and *C. albicans*, the other microbes did not respond to the higher pH.

Example 7—Skin Lotion Evaluation at pH 5.5 to 8.0

Use of 3-phenyl propanol in the skin lotion formulation as set forth in Table 1 above was evaluated according to methods described in the Challenge Testing Methodology section above. In this efficacy screen study reflected in FIGS. 18 and 19, only the time intervals at 2-day and 14-day were measured, as these are critical time points for USP-51 and European Pharmacopeia. In this example, a triblend or tri-component antimicrobial composition was used comprising 3-phenyl propanol added to the model skin lotion containing both sodium benzoate and benzyl alcohol to enhance the antimicrobial activity at pH 6.5, a common pH for skin lotions. The skin lotion formulation contained 0.25 wt. % sodium benzoate and 0.25 wt. % benzyl alcohol.

Figure 18:
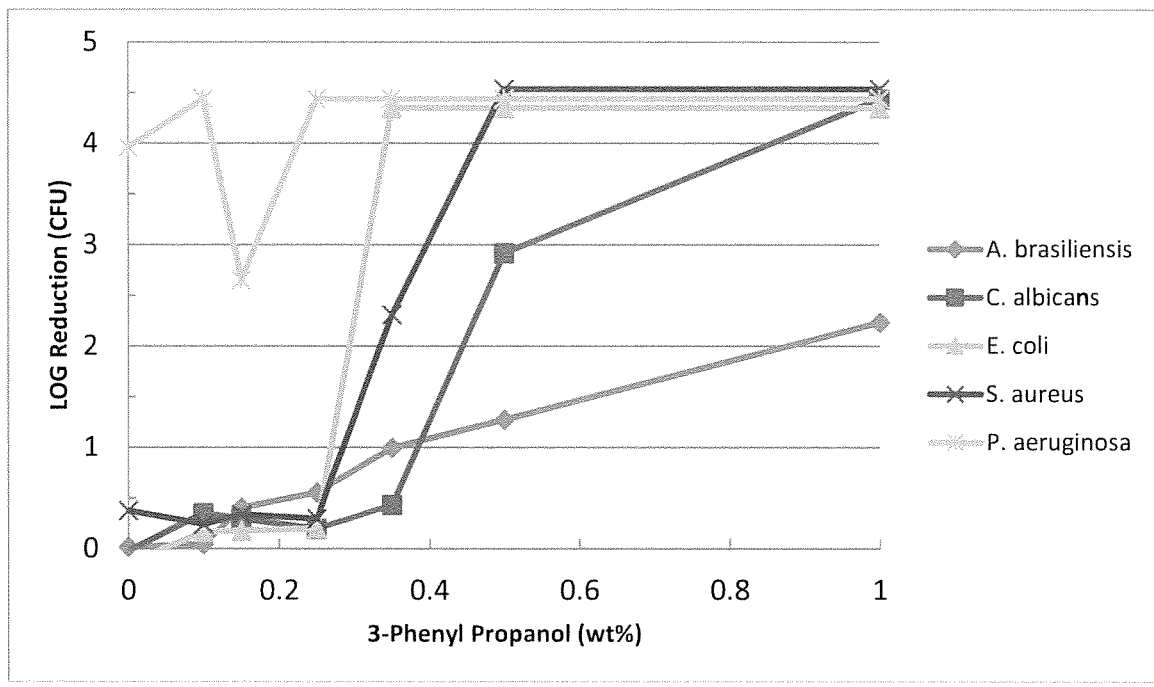

The log reduction of the microbes as shown in FIG. 18 showed that without the addition of 3-phenyl propanol (seen at 0 wt. % on graph), the skin lotion formulations would not be suitable to meet the challenging two-day, two-log reduction of *P. aeruginosa* and *S. aureus* as outlined in the European Pharmacopeia method. In this particular example, 0.35 wt. % addition of 3-phenyl propanol enhanced the antimicrobial property of the skin lotion formulation to an extent that antimicrobial performance met the two-day criteria set forth in the European Pharmacopeia.

Figure 19:
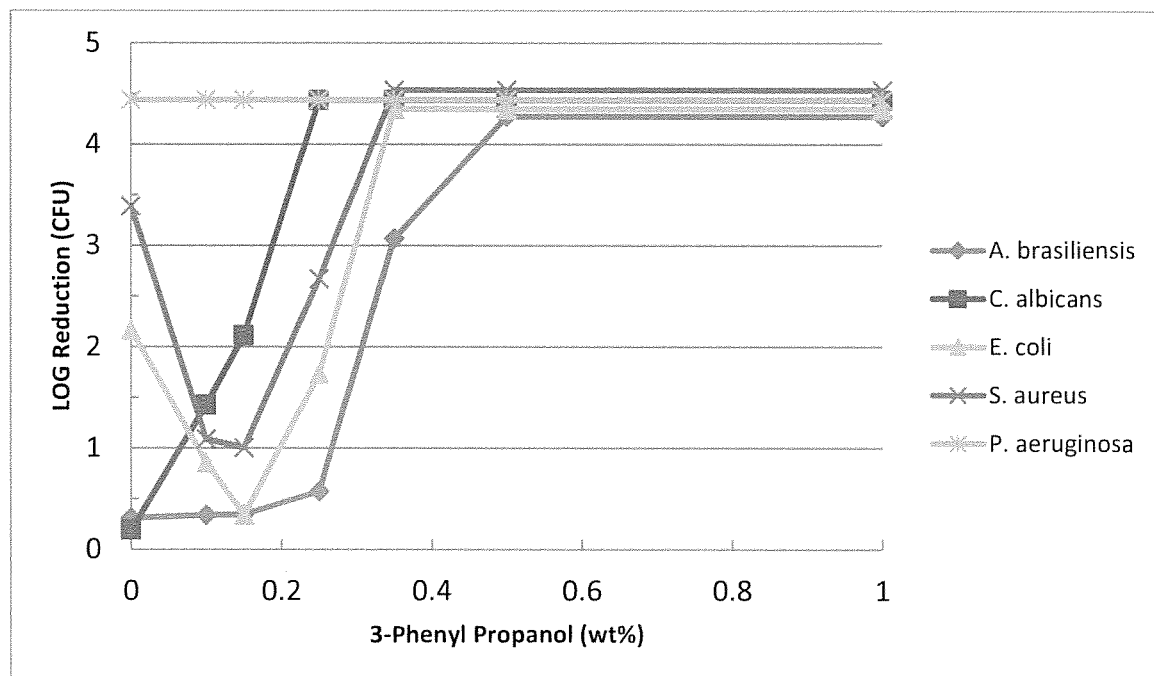
FIG. 19 reflects log reduction data for colony forming units (CFU) of microbe strains exposed to 3-phenyl propanol at various concentrations in skin lotion media at pH 6.5 after fourteen days, each skin lotion formation having a fixed concentration of 0.25 wt. % of sodium benzoate and 0.25 wt. % of benzyl alcohol, FIG. 20 reflects log reduction data for colony forming units (CFU) or *A. brasiliensis* exposed to 3-phenyl propanol and sodium benzoate (both at various concentrations) in skin lotion media at pH 5.5 after 14 days and shows a clear synergistic relationship between 3-phenyl propanol and sodium benzoate in that the log reduction of *A. brasiliensis* is enhanced with the combination of the two components as compared to that achieved with either compound alone.

The fourteen-day data depicted in FIG. 19 displayed an interesting phenomenon in that small concentrations of 3-phenyl propanol significantly decreased performance against *E. coli* and *S. aureus* after 14 days over that of the control ("0 wt. %"). Adequate antimicrobial performance under European Pharmacopeia criteria was not attained until a loading of approximately 0.35 wt. % of 3-phenyl propanol achieved the required 14-day efficacy versus bacteria, mold, and yeast as described in the Challenge Testing Methodology section above. This data strongly indicated that an ideal ratio or concentration of 3-phenyl propanol to sodium benzoate and/or benzyl alcohol is needed to achieve optimum performance under European Pharmacopeia standards and USP-51.

Based on the results observed, a synergistic tri-component antimicrobial composition, consisting of 3-phenyl propanol, 2-methyl-3-phenyl propanol in combination with an organic acid or salt thereof and an alcohol achieves enhanced antimicrobial performance at a lower total wt. % loading than a dual component mixture consisting of the antimicrobial composition of claim 1 in combination with an organic acid or salt thereof or an alcohol.

Figure 20:
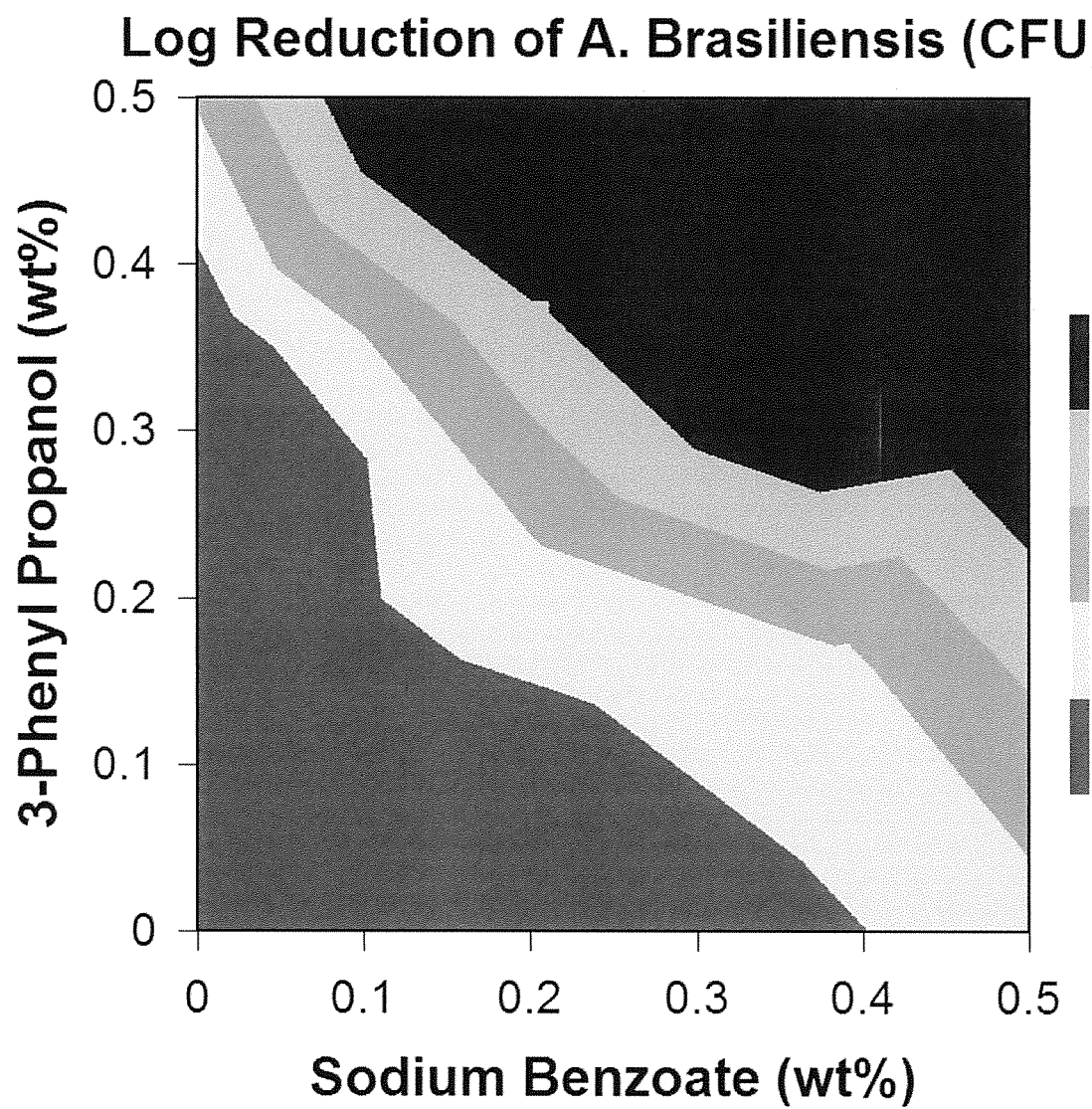

In FIG. 20, use of 3-phenyl propanol in the skin lotion set forth in Table 1 above was evaluated according to methods described in the Challenge Testing Methodology section for response of *A. brasiliensis*. In this example, 3-phenyl propanol was added to the model skin lotion with only sodium benzoate to enhance the antimicrobial activity at pH 5.5. In FIG. 20, the fourteen-day log reduction of colony forming units (CFU) for *A. brasiliensis* is reported. FIG. 20 shows a clear synergistic relationship between 3-phenyl propanol and sodium benzoate in that log reduction of *A. brasiliensis* was enhanced with the combination of the two components as compared to that achieved with either compound alone.

Figure 21:
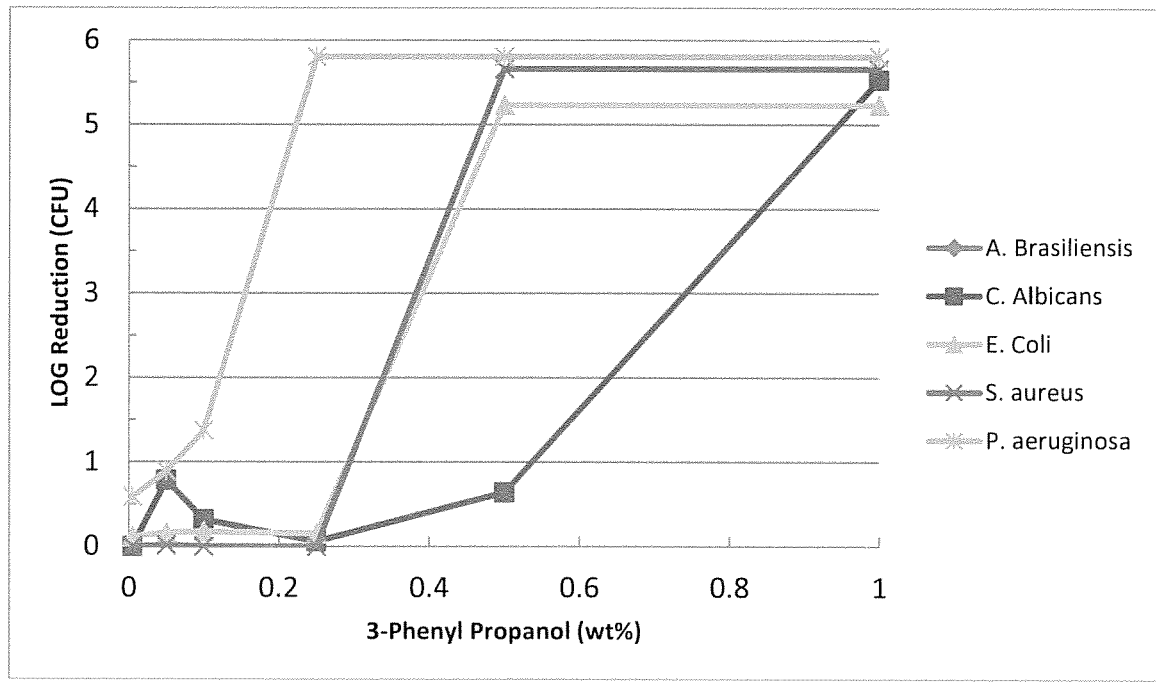
FIG. 21 reflects log reduction data for colony forming units (CFU) of microbe strains exposed to 3-phenyl propanol at various concentrations in skin lotion media at pH 6.5 after two days, each skin lotion formation having a fixed concentration of 0.5 wt. % sodium benzoate.
Figure 22:
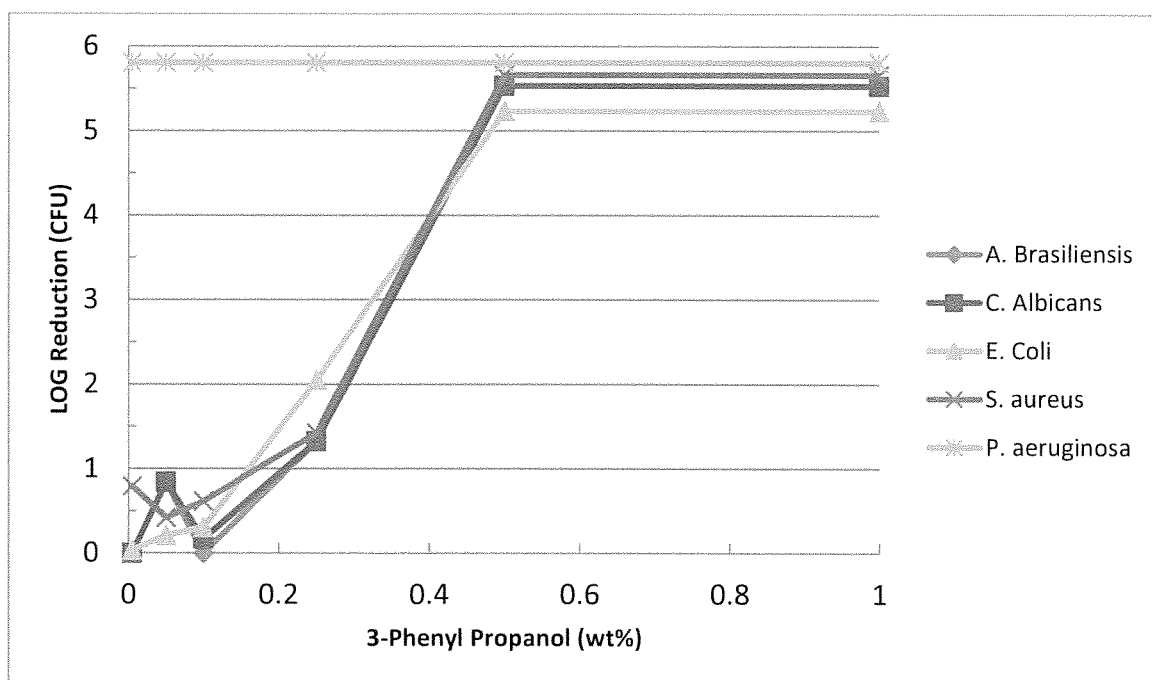
FIG. 22 reflects log reduction data for colony forming units (CFU) of microbe strains exposed to 3-phenyl propanol at various concentrations in skin lotion media at pH 6.5 after fourteen days, each skin lotion formation having a fixed concentration of 0.5 wt. % sodium benzoate.

In FIG. 21 and FIG. 22, use of 3-phenyl propanol in the skin lotion set forth in Table 1 above was evaluated according to methods described in the Challenge Testing Methodology section using the microbes identified in Example 1. In this example, 3-phenyl propanol was added to the model skin lotion with sodium benzoate at 0.5 wt. % to enhance the antimicrobial activity at pH 6.5. In these examples, 0.5 wt. % of 3-phenyl propanol in addition to 0.5 wt. % sodium benzoate was required to pass the EP 2 day and 14-day criteria.

Figure 23:
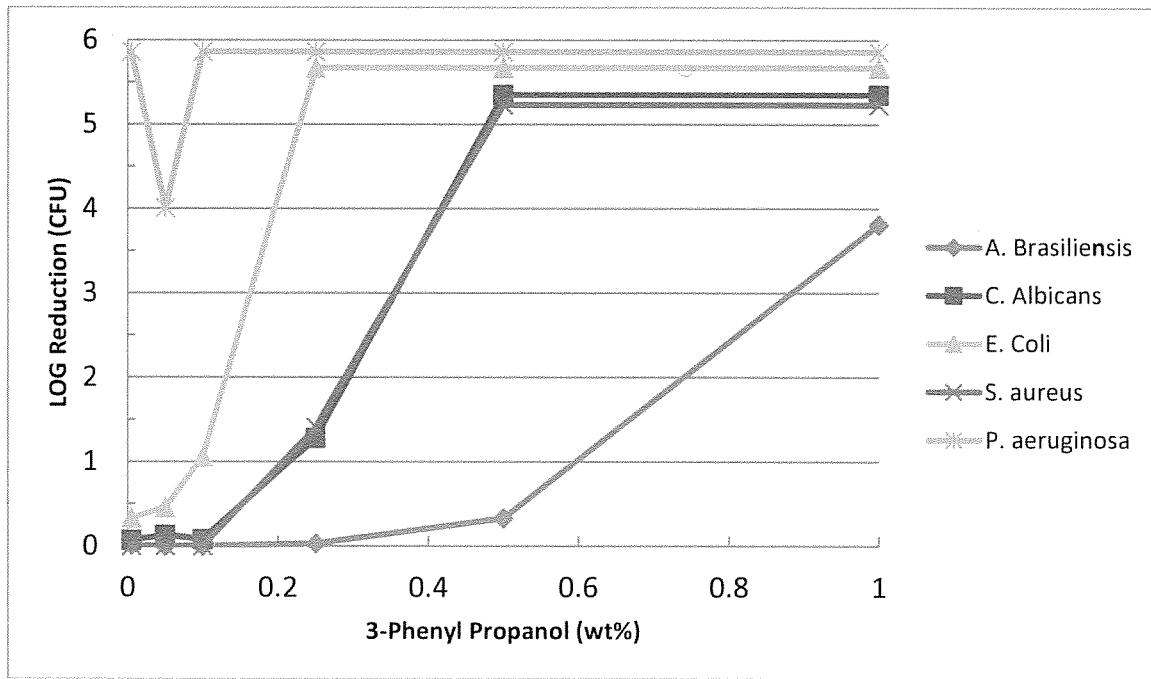
FIG. 23 reflects log reduction data for colony forming units (CFU of microbe strains exposed to 3-phenyl propanol at various concentrations in skin lotion media at pH 8.0 after two days, each skin lotion formation having a fixed concentration of 0.5 wt. % benzyl alcohol.
Figure 24:
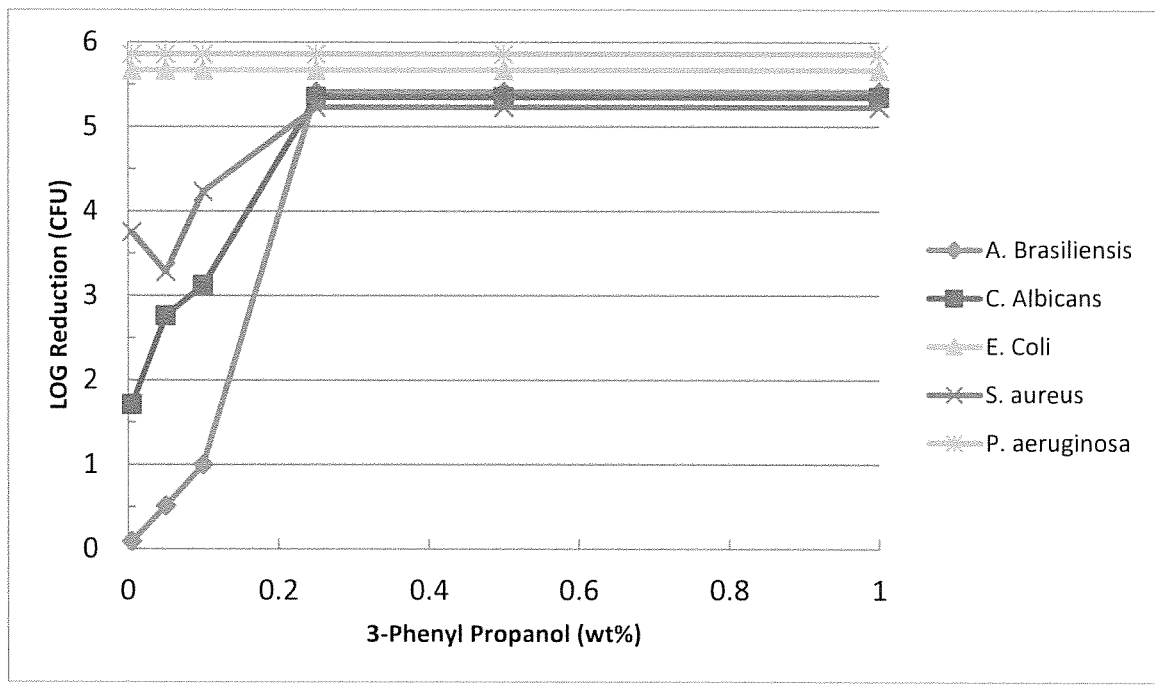
FIG. 24 reflects log reduction data for colony forming units (CFU) of microbe strains exposed to 3-phenyl propanol at various concentrations in skin lotion media at pH 8.0 after fourteen days, each skin lotion formation having a fixed concentration of 0.5 wt. % benzyl alcohol.

In FIG. 23 and FIG. 24, use of 3-phenyl propanol in the skin lotion set forth in Table 1 above was evaluated according to methods described in the Challenge Testing Methodology section above, using the microbes identified in Example 1. In this example, 3-phenyl propanol was added to the model skin lotion with benzyl alcohol at 0.5 wt. % to enhance the antimicrobial activity at pH 8.0. In these examples, 0.5 wt. % of 3-phenyl propanol in addition to 0.5 wt. % benzyl alcohol was required to pass the EP 2 day and 14-day criteria.

Figure 25:
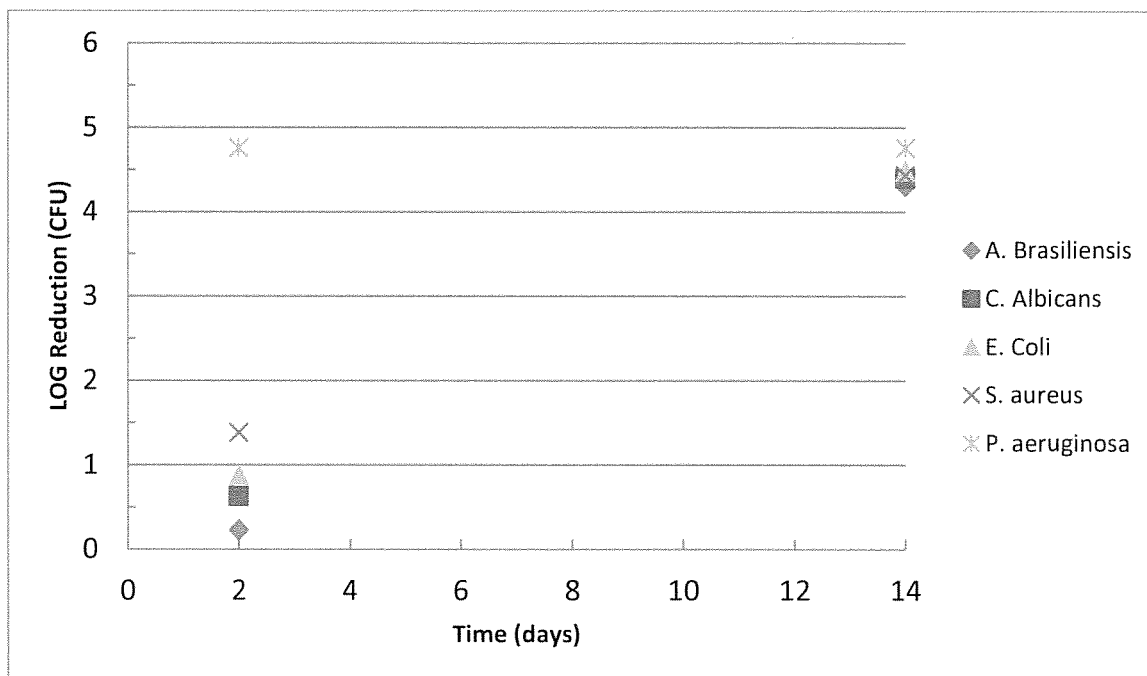
FIG. 25 reflects log reduction data for colony forming units (CFU) of microbe strains exposed to a fixed concentration of 0.5 wt. % sodium benzoate and 1 wt. % benzyl alcohol in skin lotion media at pH 6.5 at two days and fourteen days.

Use of sodium benzoate and benzyl alcohol at pH 6.5 in the skin lotion set forth in Table 1 above was evaluated according to methods described in paragraphs the Challenge Testing Methodology section above, using the microbes identified in Example 1. Again, in this case, only 2-day and 14-day time points were measured. In this example, 0.5 wt. % sodium benzoate and 1 wt. % benzyl alcohol were not sufficient to pass EP 2 day criteria. Results are set forth in FIG. 25.

FIGS. 18, 19, 21, 22, 23, 24, and 25 establish efficacy for various combinations of three components, i.e., 3-phenyl propanol combined with benzyl alcohol and/or sodium benzoate. Tri-component blends (triblends) consisted of 3-phenyl propanol, benzyl alcohol, and sodium benzoate. Dual component blends consisted of 3-phenyl propanol and benzyl alcohol or 3-phenyl propanol and sodium benzoate. A combination of 0.5 wt. % sodium benzoate and 0.5 wt. % 3-phenyl propanol was needed to pass the EP 2 day and 14 day criteria at pH 6.5 in the skin lotion formula set forth in Table 1. A combination of 0.5 wt. % benzyl alcohol and 0.5 wt. % 3-phenyl propanol was needed to pass the EP 2 day and 14 day criteria at pH 8.0 in the skin lotion formula set forth in Table 1. In the skin lotion formula of Table 1, at pH 6.5, a triblend loading concentration total of only 0.85 wt. % (0.35 wt. % 3-phenyl propanol, 0.25 wt. % sodium benzoate, and 0.25 wt. % benzyl alcohol) was required to pass the EP 2 day criteria. A combination of 0.5 wt. % sodium benzoate and 1 wt. % benzyl alcohol was unable to pass the EP 2 day criteria at pH 6.5 in the skin lotion formula set forth in Table 1, thus establishing the utility of adding 3-phenyl propanol.

Example 8—Waterborne Coating/Paint

The following example is a waterborne coating with a polymer emulsion binder. The addition of 2-methyl-3-phenyl propanol at concentrations ranging from 0.01 wt. % to 5.0 wt. %, along with traditional preservatives used in waterborne coatings, produces improved antimicrobial efficacy and/or preservation for the water borne coating or paint as compared to that achieved with the use of preservatives traditionally used in this application, including without limitation benzoisothiazolinone, methylisothiazolinone or methylchloroisothiazolinone alone. Improved efficacy may mean using less of the traditional preservatives. An exemplary waterborne coating formulation using 2-methyl-3-phenyl propanol according to the invention is set forth below in Table 2.

TABLE 2

Waterborne Coating

| Component | Weight (lb) | Function |
|---|---|---|
| Grind | | |
| Water | 107 | Carrier |
| Tamol 851 | 10 | Dispersant |
| Byk 28 | 2 | Defoamer |
| Kronos TiO$_2$ | 487 | Pigment |
| Letdown | | |
| Water | 52 | Carrier |
| Raycryl 1207 | 330 | Polymer Emulsion Binder |
| Coalescent | 10 | Coalescent |
| 2-Methyl-3-phenyl propanol | 10 | Antimicrobial |
| Preservative | Q.S. | Preservative |
| Natrosol HBR | 2 | Rheology Modifier |

Example 9—Laundry Detergent

The following example is a laundry detergent with enzymes for enhanced soil removal. The addition of 3-phenyl propanol at the use level listed below produces improved antimicrobial efficacy and/or preservation for the laundry detergent formulation as compared to that achieved with traditional preservatives alone. Improved efficacy may mean using less of the traditional preservatives.

TABLE 3

Laundry Detergent

| Component | Wt. % | Function |
|---|---|---|
| Deionized Water | Q.S. | Carrier |
| Propylene Glycol | 7.0 | Solvent |
| ALPHA-STEP MC-48 | 6.0 | Surfactant |
| BIO-SOFT N25-7 | 11.3 | Surfactant |
| STEOL CS-330 | 9.8 | Surfactant |
| Boric Acid | 2.6 | Enzyme Stabilization |
| Calcium Chloride | 0.04 | Rheology Modifier |
| Sodium Hydroxide | Q.S. | pH adjust |
| Protease | 0.5 | Enzyme |
| Lipase | 1.0 | Enzyme |
| 3-Phenyl propanol | 0.5 | Antimicrobial |
| Preservative | Q.S. | Preservative |
| Sodium Chloride | 5.0 | Rheology Modifier |

Example 10—Household Cleaner

The following example is a household cleaner formulation. The addition of 3-phenyl propanol at the use level listed below, along with traditional preservatives used in household cleaners, produces improved antimicrobial efficacy and/or preservation for the household cleaner formulation as compared to that achieved with traditional preservatives alone. Improved efficacy may mean using less of the traditional preservatives.

TABLE 3

Household Cleaner

| Component | Wt. % | Function |
|---|---|---|
| Water | Q.S. | Carrier |
| Citric Acid | 1.0% | Chelator |
| Glycerin | 2.5% | Solvent |
| Stepanol DCFAS-N | 1.33% | Surfactant |
| 3-Phenyl propanol | 0.5% | Antimicrobial |
| Preservative | Q.S. | Preservative |

While in accordance with the patent statutes the best mode and preferred embodiment have been set forth, the scope of the invention is not limited thereto, but rather by the scope of the attached claims.

What is claimed is:

1. A method of preserving a product formulation, comprising adding 3-phenyl propanol and an organic acid or salt thereof to the product formulation, wherein the 3-phenyl propanol is added in an amount constituting at least 0.2 wt. %, based on the total weight of the product formulation;

the organic acid or salt thereof is benzoic acid, dehydroacetic acid, acetic acid, citric acid, formic acid, sorbic acid, lactic acid, sodium benzoate, potassium benzoate, sodium citrate, potassium sorbate, sodium sorbate, sodium lactate or a mixture thereof; and said addition is sufficient to achieve a synergistic 14-day antimicrobial effect according to European Pharmacopeia 7 (EP) antimicrobial efficacy testing methodology against *Aspergillus brasiliensis*.

2. The method according to claim 1, wherein the organic acid or salt thereof is benzoic acid, sodium benzoate, potassium benzoate or a mixture thereof.

3. The method according to claim 1, wherein the product formulation is chosen from personal care products, cosmetics, toiletries, household products, laundry products, detergents, cleaners, pharmaceutical products, healthcare products, medical products, veterinary products and industrial products.

* * * * *